US012582727B2

(12) United States Patent
Lee

(10) Patent No.: US 12,582,727 B2
(45) Date of Patent: Mar. 24, 2026

(54) CHEMILUMINESCENT AND FLUORESCENT NANOPARTICLE FOR OPTICAL IMAGING OF CANCER

(71) Applicant: The Regents of the University of Colorado, a body corporate, Denver, CO (US)

(72) Inventor: Jung-Jae Lee, Aurora, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 1139 days.

(21) Appl. No.: 17/286,123

(22) PCT Filed: Oct. 15, 2019

(86) PCT No.: PCT/US2019/056357

§ 371 (c)(1),
(2) Date: Apr. 16, 2021

(87) PCT Pub. No.: WO2020/081581

PCT Pub. Date: Apr. 23, 2020

(65) Prior Publication Data

US 2021/0369876 A1 Dec. 2, 2021

Related U.S. Application Data

(60) Provisional application No. 62/746,383, filed on Oct. 16, 2018.

(51) Int. Cl.

| | |
|---|---|
| ***A61K 49/00*** | (2006.01) |
| ***A61B 5/00*** | (2006.01) |
| ***C08L 5/08*** | (2006.01) |
| ***C09K 11/06*** | (2006.01) |
| *B82Y 5/00* | (2011.01) |
| *B82Y 30/00* | (2011.01) |
| *B82Y 40/00* | (2011.01) |

(52) U.S. Cl.

CPC ........ *A61K 49/0093* (2013.01); *A61B 5/0071* (2013.01); *A61K 49/0021* (2013.01); *A61K 49/0054* (2013.01); *C08L 5/08* (2013.01); *C09K 11/06* (2013.01); *B82Y 5/00* (2013.01); *B82Y 30/00* (2013.01); *B82Y 40/00* (2013.01); *C08L 2203/02* (2013.01); *C09K 2211/1475* (2013.01)

(58) Field of Classification Search

CPC .............................. A61K 49/0093; B82Y 5/00

See application file for complete search history.

(56) References Cited

U.S. PATENT DOCUMENTS

| | | | | |
|---|---|---|---|---|
| 2009/0155173 A1 | | 6/2009 | Scherman et al. | |
| 2009/0169478 A1 | | 7/2009 | Leuschner et al. | |
| 2012/0184495 A1 | * | 7/2012 | Koyakutty | B82Y 5/00 977/773 |
| 2012/0296085 A1 | | 11/2012 | Smith | |
| 2015/0087050 A1 | | 3/2015 | Cunin et al. | |

FOREIGN PATENT DOCUMENTS

| | | | | | |
|---|---|---|---|---|---|
| JP | 2003081977 A | * | 3/2003 | | |
| KR | 20100051163 A | * | 5/2010 | A61K 41/0057 | |
| KR | 10-2012-0089913 A | | 8/2012 | | |
| WO | 2008091465 A2 | | 7/2008 | | |
| WO | WO-2013009701 A2 | * | 1/2013 | A61K 31/663 | |

OTHER PUBLICATIONS

International Search Report and Written Opinion dated Jan. 7, 2020 for International Appln. No. PCT/US2019/056357.

Albanese, et al., "The effect of nanoparticle size, shape, and surface chemistry on biological systems", Annual review of biomedical engineering; 14, Epub Apr. 25, 2012. doi:10.1146/annurev-bioeng-071811-150124. PubMed PMID: 22524388., Jan. 16, 2012.

Benz, et al., "Controlled oxygen release from pyridone endoperoxides promotes cell survival under anoxic conditions.", Journal of medicinal chemistry; 56(24), Epub Dec. 5, 2013. doi:10.1021/jm4016137. PubMed PMID: 24299550, 2013, 10171-82.

Buckland, "Experimental arthritis: in vivo noninvasive molecular optical imaging of disease.", Nature reviews Rheumatology; 11(5); Epub Mar. 25, 2015. doi: 10.1038/nrrheum.2015.39. PubMed PMID: 25800213., 2015, 258.

Bulte, et al., "Iron oxide MR contrast agents for molecular and cellular imaging.", NMR in biomedicine; 17(7); Epub Nov. 5, 2004. doi: 10.1002/nbm.924. PubMed PMID: 15526347., 2004, 484-99.

Cheng, et al., "Upconversion nanoparticles and their composite nanostructures for biomedical imaging and cancer therapy", Nanoscale, vol. 5 (DOI: 10.1039/c2nr32311g), 2013, pp. 23-37.

Filatov, et al., "Molecular devices based on reversible singlet oxygen binding in optical and photomedical applications", Mol Syst Des Eng, vol. 1, No. 3 (DOI: 10.1039/c6me00042h), Oct. 2016, pp. 258-272.

Gazeau, et al., "Optimizing magnetic nanoparticle design for nanothermotherapy.", Nanomedicine (London, England); 3(6). Epub Nov. 26, 2008. doi: 10.2217/17435889.3.6.831. PubMed PMID: 19025457., 2008, 831-44.

Gupta, et al., "Synthesis and surface engineering of iron oxide nanoparticles for biomedical applications.", Biomaterials., 26(18), Epub Jan. 1, 2005. doi: 10.1016/j.biomaterials.2004.10.012. PubMed PMID: 15626447., 2005, 3995-4021.

(Continued)

*Primary Examiner* — James W Rogers

(74) *Attorney, Agent, or Firm* — Saul Ewing LLP; Domingos J. Silva; Dennis Ostrovsky

(57) ABSTRACT

The present invention provides compositions and methods for detecting tumor tissues in a subject. Embodiments of the present invention provide biocompatible chitosan nanoparticles suitable for dual modality optical imaging. Embodiments of the present invention provide methods for fabricating chitosan nanoparticles. Embodiments of the present invention provide methods for detecting tumor tissues in a subject using compositions provided by the present invention.

10 Claims, 19 Drawing Sheets

(56) References Cited

OTHER PUBLICATIONS

Huang, et al., "Uptake and cytotoxicity of chitosan molecules and nanoparticles: effects of molecular weight and degree of deacetylation.", Pharm Res., 21(2); Epub Mar. 23, 2004. PubMed PMID: 15032318., 2004, 344-53.
Kelderhouse, et al., "Low PS. Development of tumortargeted near infrared probes for fluorescence guided surgery.", Bioconjugate chemistry, 24(6), Epub May 7, 2013. doi: 10.1021/bc400131a. PubMed PMID: 23642154., 2013, 1075-80.
Key, et al., "Multicomponent, Tumor-Homing Chitosan Nanoparticles for Cancer Imaging and Therapy", Intl J Mol Sci, vol. 18, No. 594 (DOI: 10.3390/ijms18030594), Mar. 8, 2017, pp. 1-19.
Kiessling, et al., "Nanoparticles for imaging: top or flop?", Radiology; 273(1), Epub Sep. 24, 2014. doi: 10.1148/radiol.14131520. PubMed PMID: 25247562; PMCID: PMC4186876., Oct. 28, 2014.
Kularatne, et al., "Low PS. Design, synthesis, and preclinical evaluation of prostate-specific membrane antigen targeted (99m)Tc-radioimaging agents.", Mol Pharm.; 6(3); Epub Apr. 14, 2009. doi: 10.1021/mp9000712. PubMed PMID: 19361232., 2009, 790-800.
Kularatne, et al., "Low PS. Prostate-specific membrane antigen targeted imaging and therapy of prostate cancer using a PSMA inhibitor as a homing ligand.", Mol Pharm, 6(3), Epub Apr. 14, 2009. doi: 10.1021/mp900069d. PubMed PMID: 19361233., 2009, 780-9.
Laconte, et al., "Coating thickness of magnetic iron oxide nanoparticles affects R2 relaxivity.", Journal of magnetic resonance imaging : JMRI; 26(6), Epub Oct. 31, 2007. doi: 10.1002/jmri.21194. PubMed PMID: 17968941., 2007, 1634-41.
Leamon, et al., "Comparative preclinical activity of the folate-targeted Vinca alkaloid conjugates EC140 and EC145.", International journal of cancer; 121(7); Epub Jun. 7, 2007. doi: 10.1002/ijc.22853. PubMed PMID: 17551919., 2007, 1585-92.
Leamon, et al., "Synthesis and biological evaluation of EC140: a novel folate-targeted vinca alkaloid conjugate.", Bioconjugate chemistry; 17(5); Epub Sep. 21, 2006. doi: 10.1021/bc060145g. PubMed PMID: 16984132., 2006, 1226-32.
Lee, et al., "Synthetic ligand-coated magnetic nanoparticles for microfluidic bacterial separation from blood.", Nano Lett.; 14(1); doi: 10.1021/nl3047305. PubMed PMID: 23367876., Jan. 5, 2014.
Molday, et al., "Immunospecific ferromagnetic iron-dextran reagents for the labeling and magnetic separation of cells.", Journal of immunological methods; 52(3), Epub Aug. 13, 1982. PubMed PMID: 7130710., 1982, 353-67.
Moore, et al., "Uptake of dextran-coated monocrystalline iron oxides in tumor cells and macrophages. Journal of magnetic resonance imaging", JMRI; 7(6); Epub Dec. 24, 1997. PubMed PMID: 9400860., 1997, 1140-5.
Nahrendorf, et al., "Hybrid PET-optical imaging using targeted probes.", Proceedings of the National Academy of Sciences of the United States of America; 07(17); Epub Apr. 14, 2010. doi: 10.1073/pnas.0915163107. PubMed PMID: 20385821; PMCID: PMC2867879., 2010, 7910-5.
Park, et al., "Magnetic Iron Oxide Nanoworms for Tumor Targeting and Imaging.", Advanced materials (Deerfield Beach, Fla); 20(9), Epub May 5, 2008. doi: 10.1002/adma.200800004. PubMed PMID: 21687830; PMCID: PMC3115756., 2008, 1630-5.
Parveen, et al., "Long circulating chitosan/PEG blended PLGA nanoparticle for tumor drug delivery.", European journal of pharmacology; 670(2-3); Epub Sep. 29, 2011. doi: 10.1016/j.ejphar.2011.09.023. PubMed PMID: 21951969., 2011, 372-83.
Poselt, et al., "Relaxivity optimization of a PEGylated iron-oxide-based negative magnetic resonance contrast agent for T(2)-weighted spin-echo imaging", ACS nano.; 6(2); Epub Jan. 27, 2012. doi: 10.1021/nn204591r. PubMed PMID: 22276942., 2012, 1619-24.
Raynal, et al., "Macrophage endocytosis of superparamagnetic iron oxide nanoparticles: mechanisms and comparison of ferumoxides and ferumoxtran-10.", Investigative radiology, 39(1), Epub Jan. 1, 2004. doi: 10.1097/01.rli.0000101027.57021.28. PubMed PMID: 14701989., 2004, 56-63.
Simberg , et al., "Differential proteomics analysis of the surface heterogeneity of dextran iron oxide nanoparticles and the implications for their in vivo clearance.", Biomaterials, 30(23-24), Epub Apr. 28, 2009. doi: 10.1016/j.biomaterials.2009.03.056. PubMed PMID: 19394687; PMCID: PMC2792080., 2009, 3926-33.
Stylianopoulos, et al., "EPR-effect: utilizing size-dependent nanoparticle delivery to solid tumors.", Therapeutic delivery; 4(4); Epub Apr. 6, 2013. doi: 10.4155/tde.13.8. PubMed PMID: 23557281., 2013, 421-3.
Thorek, et al., "Superparamagnetic iron oxide nanoparticle probes for molecular imaging.", Annals of biomedical engineering, 34(1), Epub Feb. 24, 2006. doi: 10.1007/s10439-005-9002-7. PubMed PMID: 16496086., 2006, 23-38.
Vlahov, et al., "Design and regioselective synthesis of a new generation of targeted chemotherapeutics. Part 1: EC145, a folic acid conjugate of desacetylvinblastine monohydrazide.", Bioorg Med Chem Lett. 2006;16(19):5093-6. Epub Jul. 28, 2006. doi: 10.1016/j.bmcl.2006.07.030. PubMed PMID: 16870437., 2006, 5093-6.
Wang, et al., "High-relaxivity superparamagnetic iron oxide nanoworms with decreased immune recognition and long-circulating properties.", ACS nano.; 8(12), Epub Nov. 25, 2014. doi: 10.1021/nn505126b. PubMed PMID: 25419856; PMCID: PMC4692719., 2014, 12437-49.
Wu, et al., "In vivo leukocyte labeling with intravenous ferumoxides/protamine sulfate complex and in vitro characterization for cellular magnetic resonance imaging.", American journal of physiology Cell physiology; 293(5), Epub Sep. 28, 2007. doi: 10.1152/ajpcell.00215.2007. PubMed PMID: 17898131., 2007, C1698-708.
Wunderbaldinger, et al., "Crosslinked iron oxides (CLIO): a new platform for the development of targeted MR contrast agents.", Academic radiology, 9 Suppl 2:S304-6. Epub Aug. 22, 2002. PubMed PMID: 12188255., 2002.
Yoon, et al., "Glycol chitosan nanoparticles as specialized cancer therapeutic vehicles: Sequential delivery of doxorubicin and Bcl-2 siRNA", Scientific Reports, 4, Article No. 6878 (DOI: 10.1038/srep06878), Nov. 3, 2014, pp. 1-12.
Yoon, et al., "Multicore assemblies potentiate magnetic properties of biomagnetic nanoparticles.", Advanced materials (Deerfield Beach, Fla); 23(41); Epub Sep. 29, 2011. doi: 10.1002/adma.201102948. PubMed PMID: 21953810; PMCID: PMC3224986., 2011, 4793-7.

* cited by examiner

| | $R_1$ | $R_2$ | $R_3$ | $R_4$ | $T_{1/2}$, h (in $H_2O$) |
|---|---|---|---|---|---|
| Py-EP1 | H | H | H | H | 0.5 |
| Py-EP2 | H | H | H | $CH_3$ | 8.5 |
| Py-EP3 | $CH_3$ | H | H | H | 4 |
| Py-EP4 | H | $CH_3$ | H | $CH_3$ | 13 |
| Py-EP5 | $CH_3$ | H | H | $CH_3$ | 4 |
| Py-EP6 | $CH_3$ | $CH_3$ | H | $CH_3$ | 15 |

700

S701  Couple chlorin e6 to glycol chitosan under suitable reaction conditions

S702  Couple small-molecule ligand to glycol chitosan under suitable reaction conditions S703  Couple derivatized singlet oxygen releasing agent to the Ce6-coupled glycol chitosan under suitable reaction conditions S704  Isolate the resulting glycol chitosan that is coupled to chlorin e6, small-molecule ligand and derivatized singlet oxygen releasing agent S705  Irradiate the glycol chitosan that is coupled to chlorin e6 and derivatized singlet oxygen releasing agent

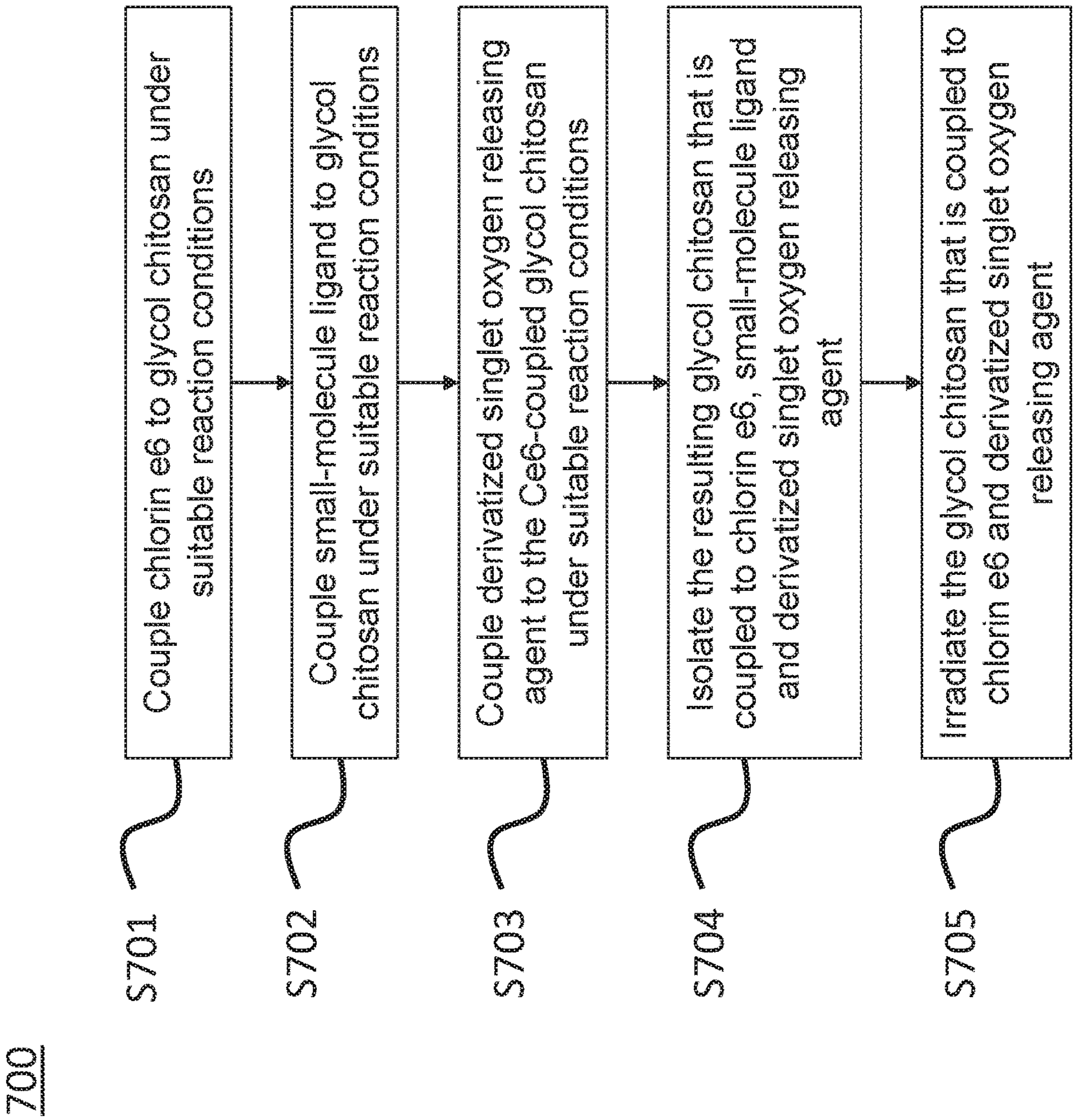

Administer CNPs to a subject

S802

Image the subject using a suitable fluorescence and/or luminescence detector

S803

Detect a positive signal from the CNPs in the tissue of interest relative to a comparator control.

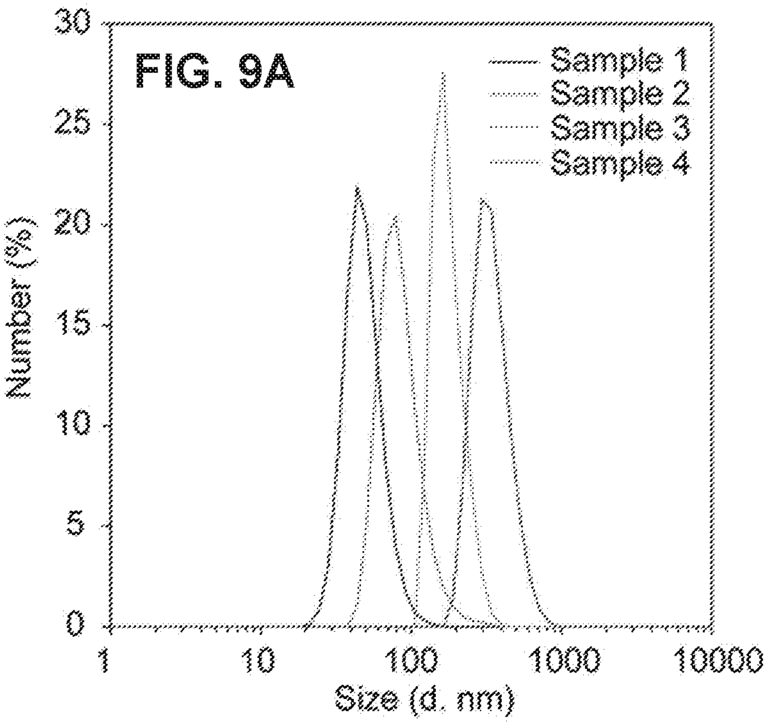
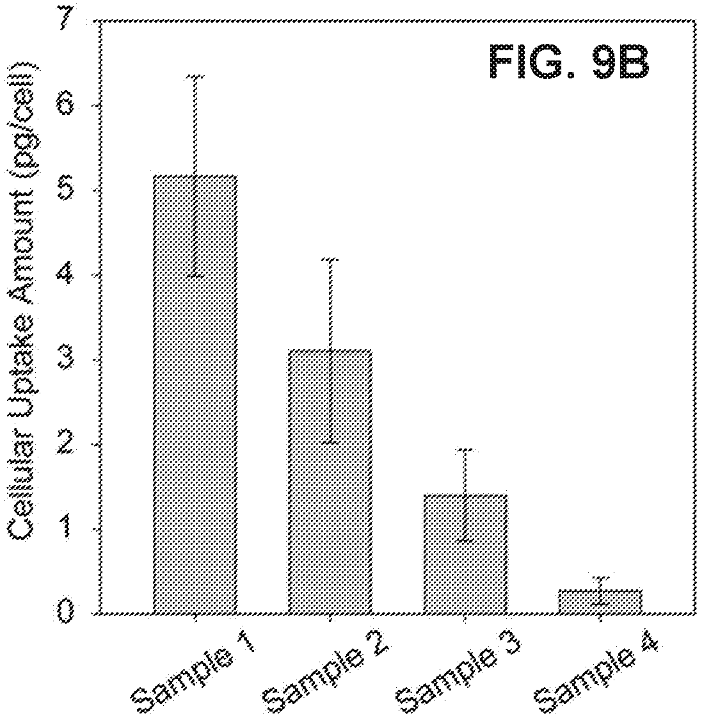
FIG. 9C
| Sample | Incubation time (h) | Nanoparticle Size (d. nm) |
|---|---|---|
| Sample 1 | 72 | 49.6±15.1 |
| Sample 2 | 48 | 97.2±34.5 |
| Sample 3 | 24 | 178.3±50.2 |
| Sample 4 | 0 | 349.2±112.8 |

CHEMILUMINESCENT AND FLUORESCENT NANOPARTICLE FOR OPTICAL IMAGING OF CANCER

CROSS-REFERENCE TO RELATED APPLICATIONS

This application is a 35 U.S.C. § 371 national phase application from, and claims priority to, International Application No. PCT/US2019/56357, filed Oct. 15, 2019, and published under PCT Article 21(2) in English, which claims priority under 35 U.S.C. § 119(e) to U.S. Provisional Application No. 62/746,383, filed Oct. 16, 2018, the content of each of which is incorporated by reference herein in their entirety.

BACKGROUND OF THE INVENTION

The advent of in vivo molecular imaging has had a major positive impact on human health, and is particularly useful in preclinical settings. In vivo molecular imaging provides real-time information for early diagnosis, quickly determines efficacy endpoints in living subjects, and facilitates longitudinal follow-up studies of tumor development.

However, despite significant advances in conventional imaging methods (e.g., X-ray, MRI, PET, SPECT, and so forth), the following shortcomings must be addressed to further improve outcomes: 1) the radioisotopes, particularly positron emitters, tend to decay rapidly, which limits their shelf-life; 2) high-energy radiation induces ionization processes that are potentially harmful to living systems; 3) use of radioisotopes, especially for serial studies, is associated with safety concerns; and 4) techniques that employ isotopes are generally less sensitive, and more expensive than those that use non-radioactive probes.

Optical imaging is amenable to high throughput analyses because images can be acquired in a few seconds and simultaneous imaging of multiple subjects is also feasible. In contrast to other molecular imaging methods, optical imaging significantly reduces patient exposure to harmful radiation by using non-ionizing radiation and therefore it can be used for lengthy and repeated procedures over time to monitor the progression of disease or the results of treatment. Additionally, optical imaging is highly sensitive and cost effective, and the method is straightforward to use.

However, an obvious limitation is the short depth of penetration (1-20 mm), due to scattering of light by blood, tissues, and other biological components. Near-infrared fluorescence (NIR-FL, 650-900 nm) and luminescence effectively achieve deeper penetration into tissues in vivo, and are associated with low autofluorescence, reduced light scattering, and an excellent signal-to-noise ratio (SNR). In particular, the luminescence can be visualized in dark conditions without photo-excitation: bioluminescence (BL) can be amplified by enzymatic reactions (e.g., with use of luciferase). However, the requirement for substrates (e.g., D-luciferin or coelenterazine) is an important drawback and external addition of these substrates complicates the interpretation of in vivo imaging experiments. Furthermore, current BL systems emit predominantly visible light, whose penetration through heterogeneous matrices is very limited. The need for BL systems that emit red-shifted light with deep tissue penetration is well recognized. However, the red fluorescent proteins, dyes, or quantum dots with luciferase enzymes that are in current use do not produce luminescence in the absence of chemical input, nor do they display any synthetic flexibility.

There is thus a need in the art for luminescence probes that do not require a separately administered substrates. In certain embodiments, such probes possess red-shifted emission spectra in order to offer improved detection of non-superficial target tissues. The present invention addresses these unmet needs in the art.

SUMMARY OF THE INVENTION

The invention provides a biocompatible dual-modality optical imaging nanoparticle, wherein the nanoparticle comprises chitosan. In certain embodiments, the chitosan is conjugated with a photosensitizer. In certain embodiments, the chitosan is conjugated with a singlet oxygen releasing agent. In certain embodiments, the agent exists in an oxygen-free form. In certain embodiments, the agent exists in an oxygen-loaded form.

The invention provides a method of detecting or imaging a tumor in a subject. In certain embodiments, the method comprises administering to the subject an amount of at least one nanoparticle of the invention. In certain embodiments, the method comprises imaging the subject using an optical imaging detection modality. In certain embodiments, the method comprises detecting or imaging a tumor in the subject.

The invention provides a method for fabricating a dual-modality optical imaging nanoparticle. In certain embodiments, the method comprises reacting chlorin e6 (Ce6) and chitosan, under conditions that allow for coupling of Ce6 to chitosan. In certain embodiments, the method comprises reacting a derivatized singlet oxygen releasing agent with the Ce6-coupled chitosan under conditions that allow for coupling of the derivatized singlet oxygen releasing agent to the Ce6-coupled chitosan. In certain embodiments, the method comprises isolating the resulting Ce6-coupled, derivatized singled oxygen releasing agent-coupled, chitosan.

BRIEF DESCRIPTION OF THE DRAWINGS

The following detailed description of selected embodiments of the invention will be better understood when read in conjunction with the appended drawings. For the purpose of illustrating the invention, specific embodiments are illustrated in the drawings. It should be understood, however, that the invention is not limited to the precise arrangements and instrumentalities of the embodiments illustrated in the drawings.

FIG. 3A depicts an exemplary experimental set-up for planar CL. FIG. 3B depicts a CL intensity map of mouse located above the tube, which is transmitted through the mouse (SNR=21). FIG. 3C depicts a fluorescence (FL) intensity map of a mouse located above the tube (SNR=~1). FIG. 3D depicts CL (upper panel)

and FL (lower panel) imaging of the CNP solutions (6 μg/mL of Ce6) through pork tissues.

Figure 4:
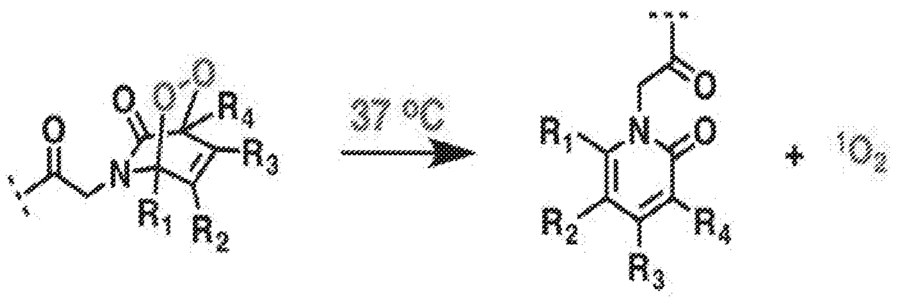

FIG. 4 depicts an exemplary schematic of $^1O_2$ release agents on exemplary Py-$EP_n$ molecules and a table of half-lives of various pyridone-derived endoperoxides (Py-EPs) in water at 37° C.

Figure 5:
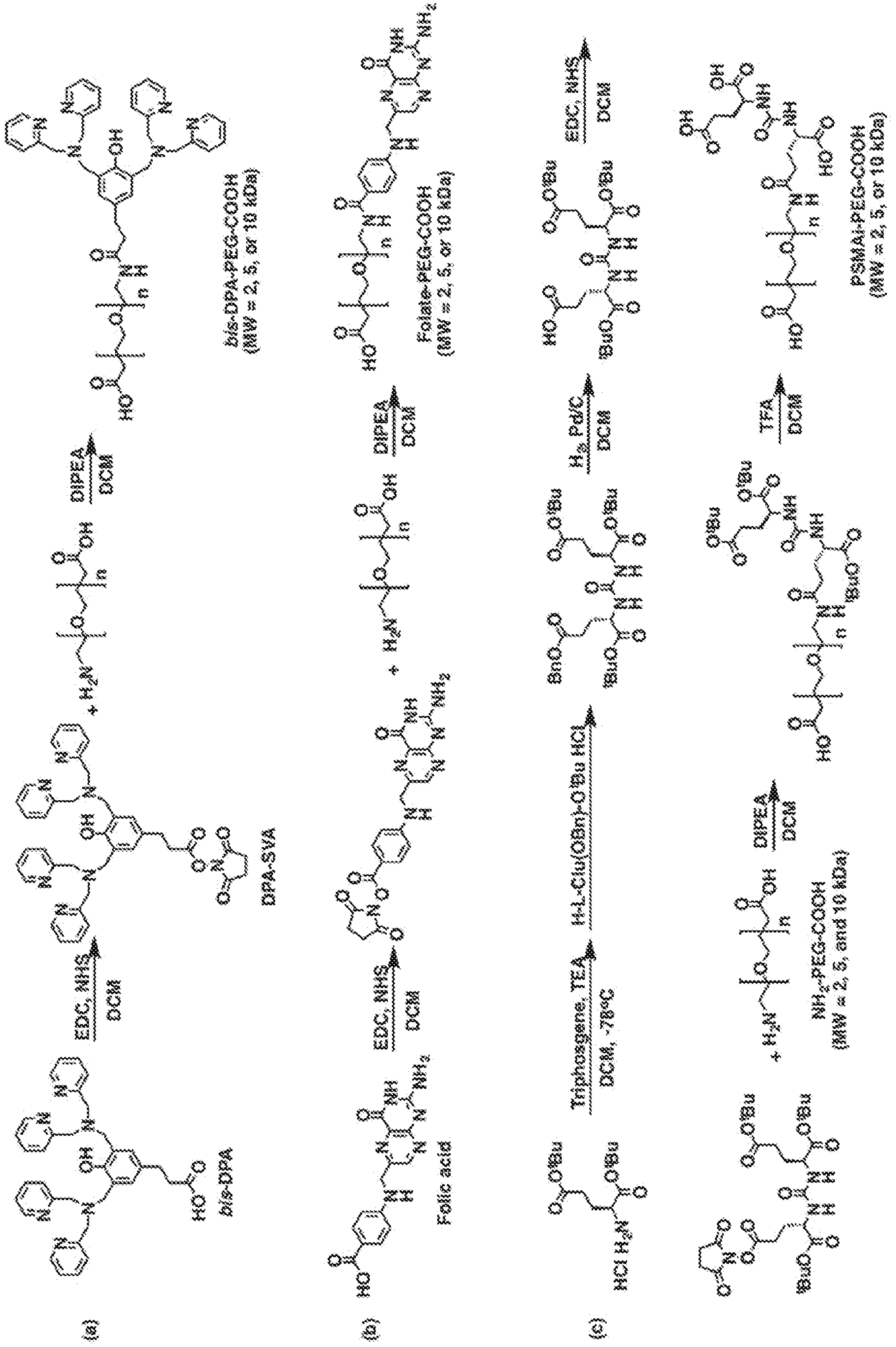

FIG. 5 depicts an exemplary scheme for the synthesis of small-molecule ligands.

Figure 6:
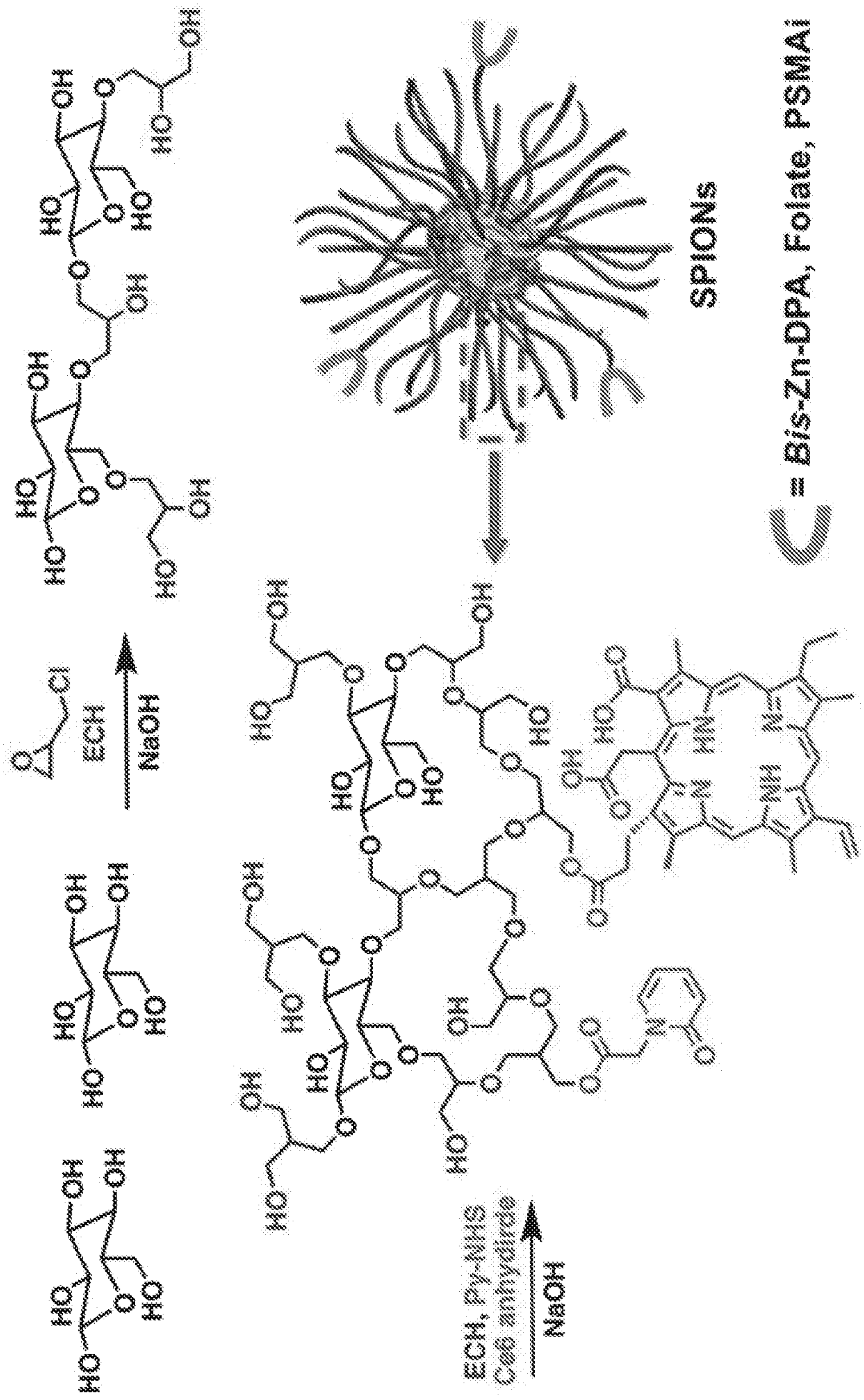

FIG. 6 depicts an exemplary scheme for the synthesis of cross-linked superparamagnetic iron oxide nanoparticles (SPIONs).

FIG. 7 depicts an exemplary method for using the compositions of the present invention for imaging a target tissue.

Figure 8:
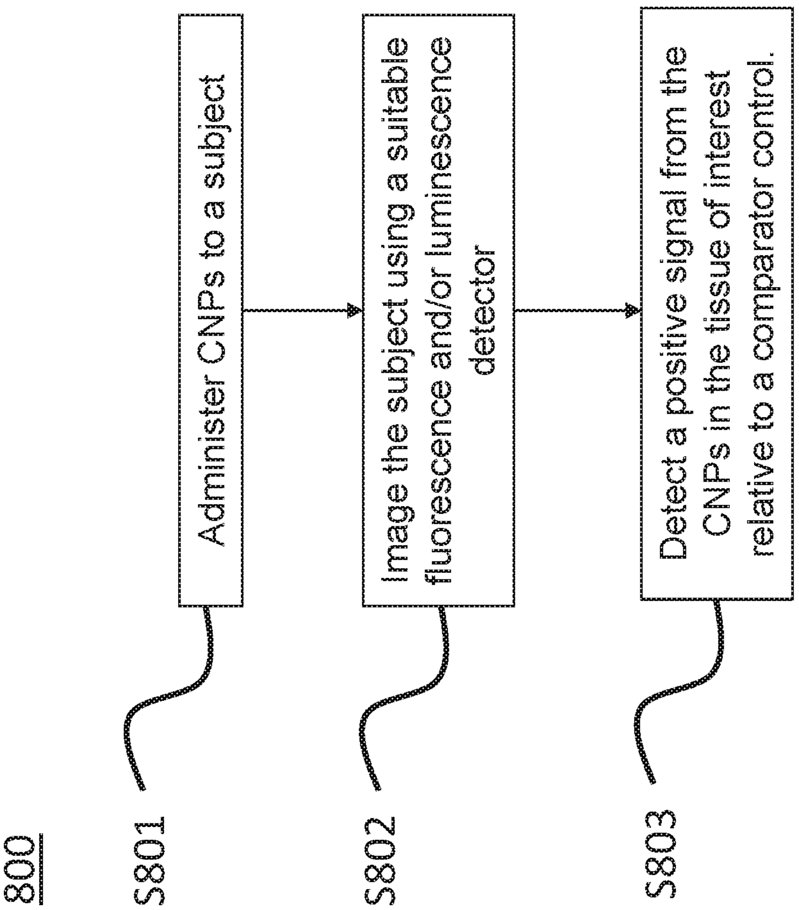

FIG. 8 depicts an exemplary method for synthesizing compositions of the present invention.

FIG. 9A depicts size distributions of CNP samples, FIG. 9B depicts cellular update data of CNP samples, and FIG. 9C depicts tabulated data about each CNP sample.

Figure 10:
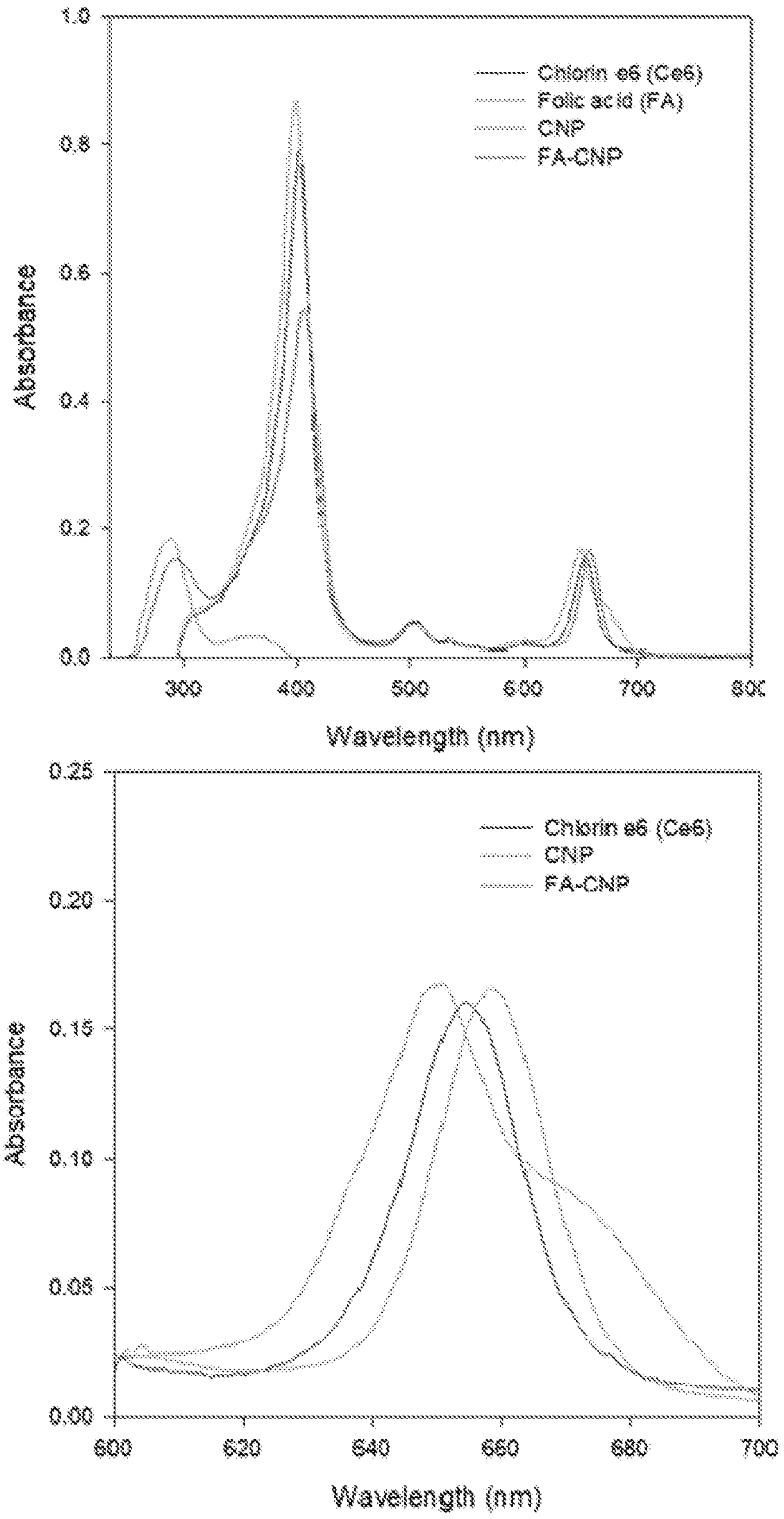
Figure 11A:
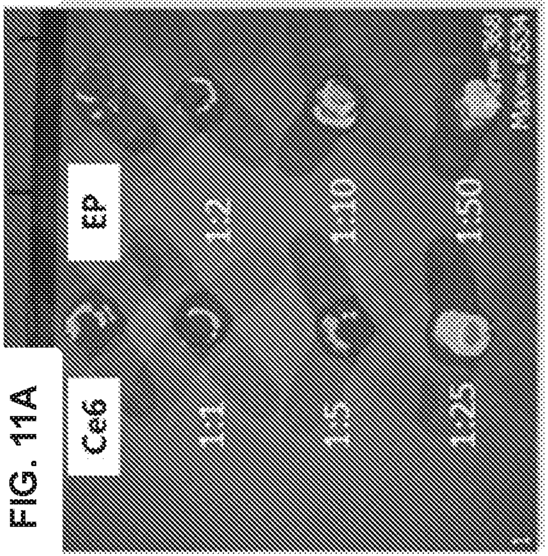
Figure 11B:
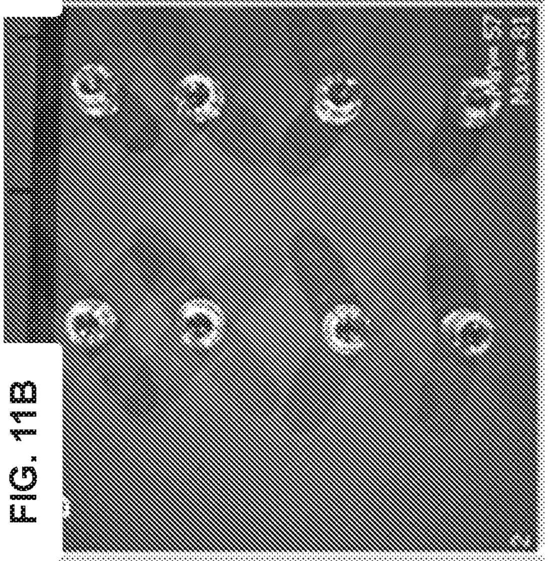
Figure 11C:
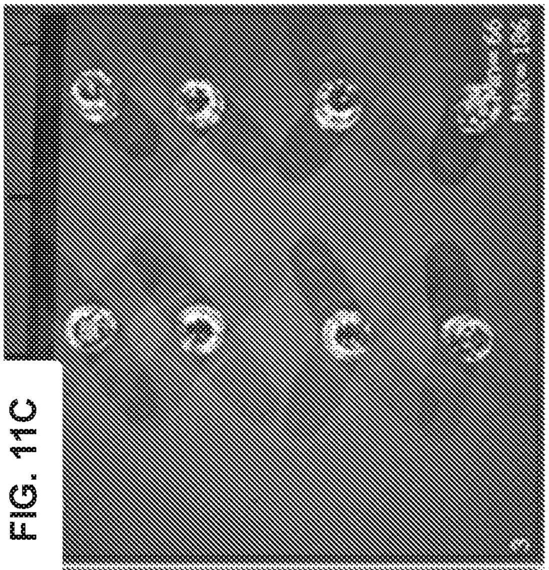
Figure 11D:
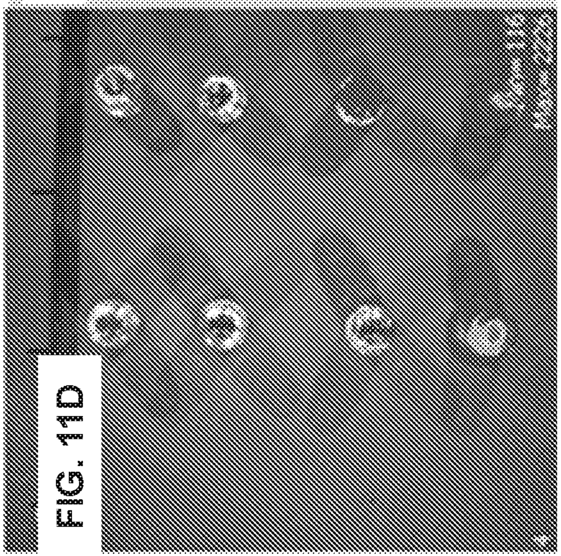
Figure 11E:

FIG. 10 depicts exemplary UV/vis spectra of chlorin e6 (Ce6), folic acid (FA), CNP and FA-CNP in DMSO.

FIGS. 11A-11E depict CL studies of 100 μM Chlorin e6 (Ce6) and varying ratios of endoperoxide (EP) in deuterated 1,1,2,2-tetrachloroethane. Emission was detected under open (FIG. 11A), GFP (FIG. 11B), DS RED (FIG. 11C), Cy 5.5 (FIG. 11D), and ICG (FIG. 11E), filters at 0 min after chamber had reached 37° C.

Figure 12:
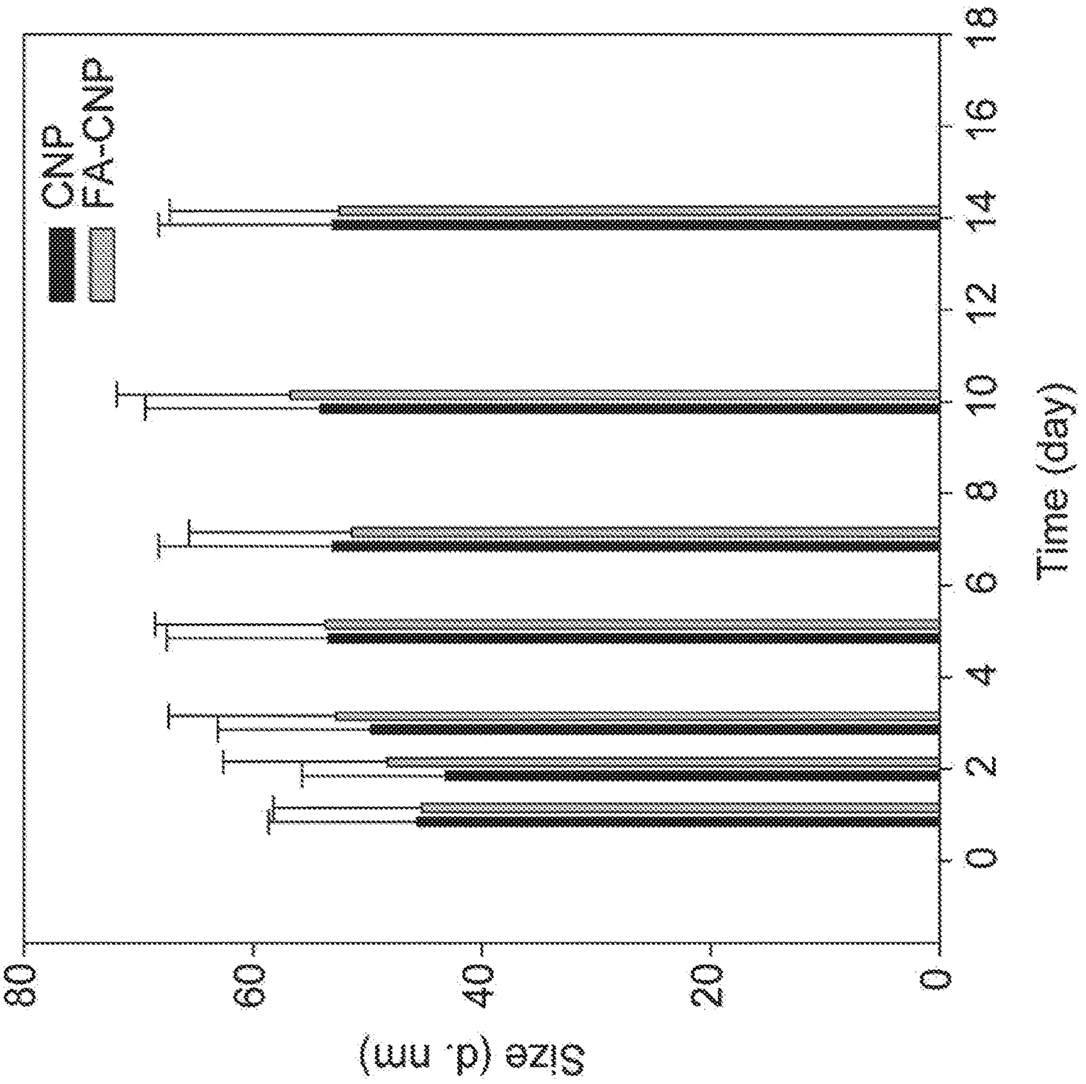

FIG. 12 illustrates the variation in sizes of CNP and FA-CNP in PBS containing 20% fetal bovine serum that were evaluated for 14 days.

Figures 13A, 13B, 13C, 13D:
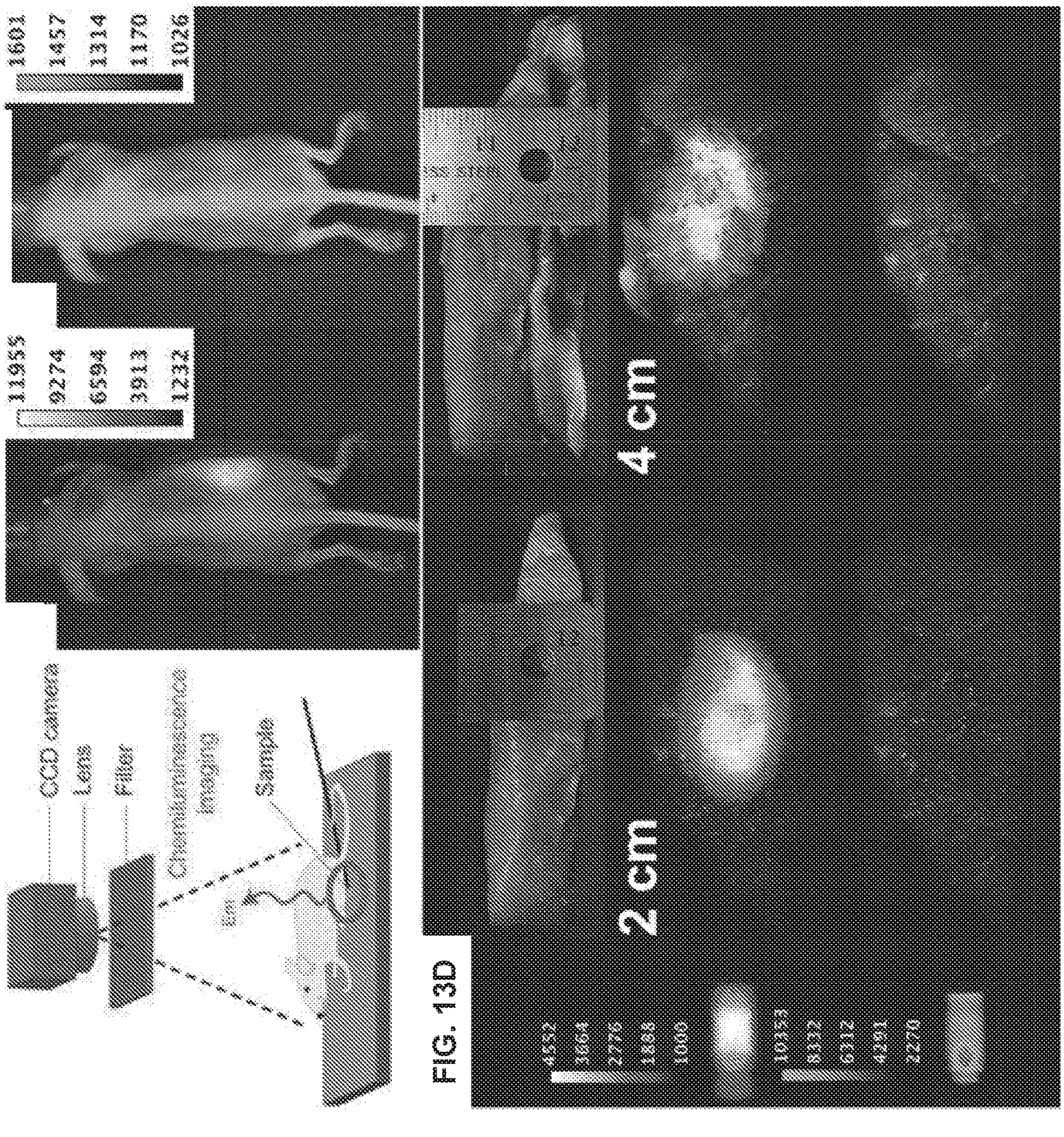

FIGS. 13A-13D demonstrate that CL from CNPs at 37° C. penetrates through a living nude mouse and pork tissues (>4 cm). FIG. 13A depicts experimental set-up for planar CL.

FIG. 13B depicts a CL intensity map of mouse located above the tube, which is transmitted through the mouse (SNR=21). FIG. 13C depicts a FL intensity map of mouse located above the tube (SNR=~1). FIG. 13D depicts CL (upper panel) and FL (lower panel) imaging of the CNP solutions (6 μg/mL of Ce6) through pork tissues.

Figure 14A:
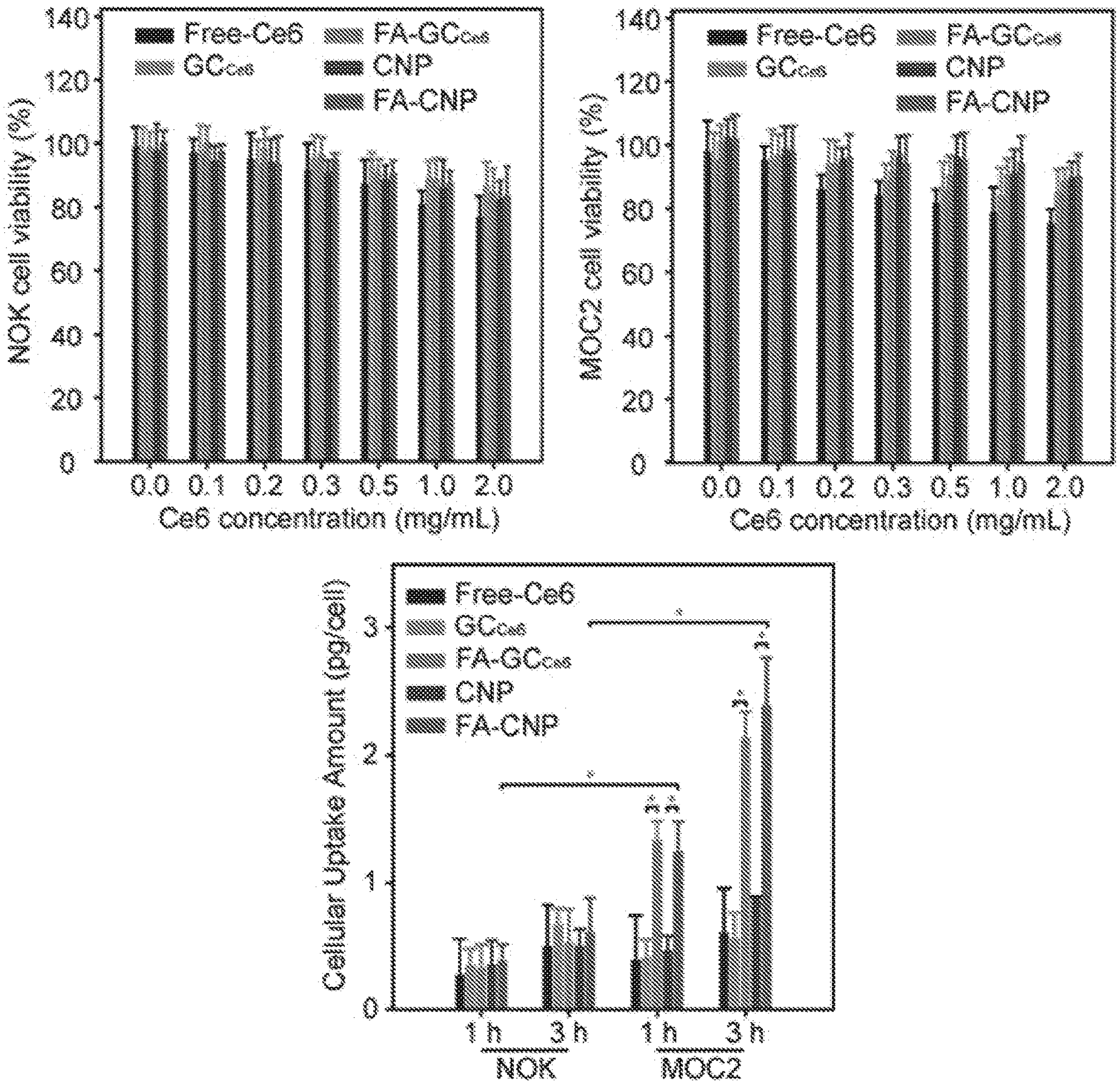
Figure 14B:
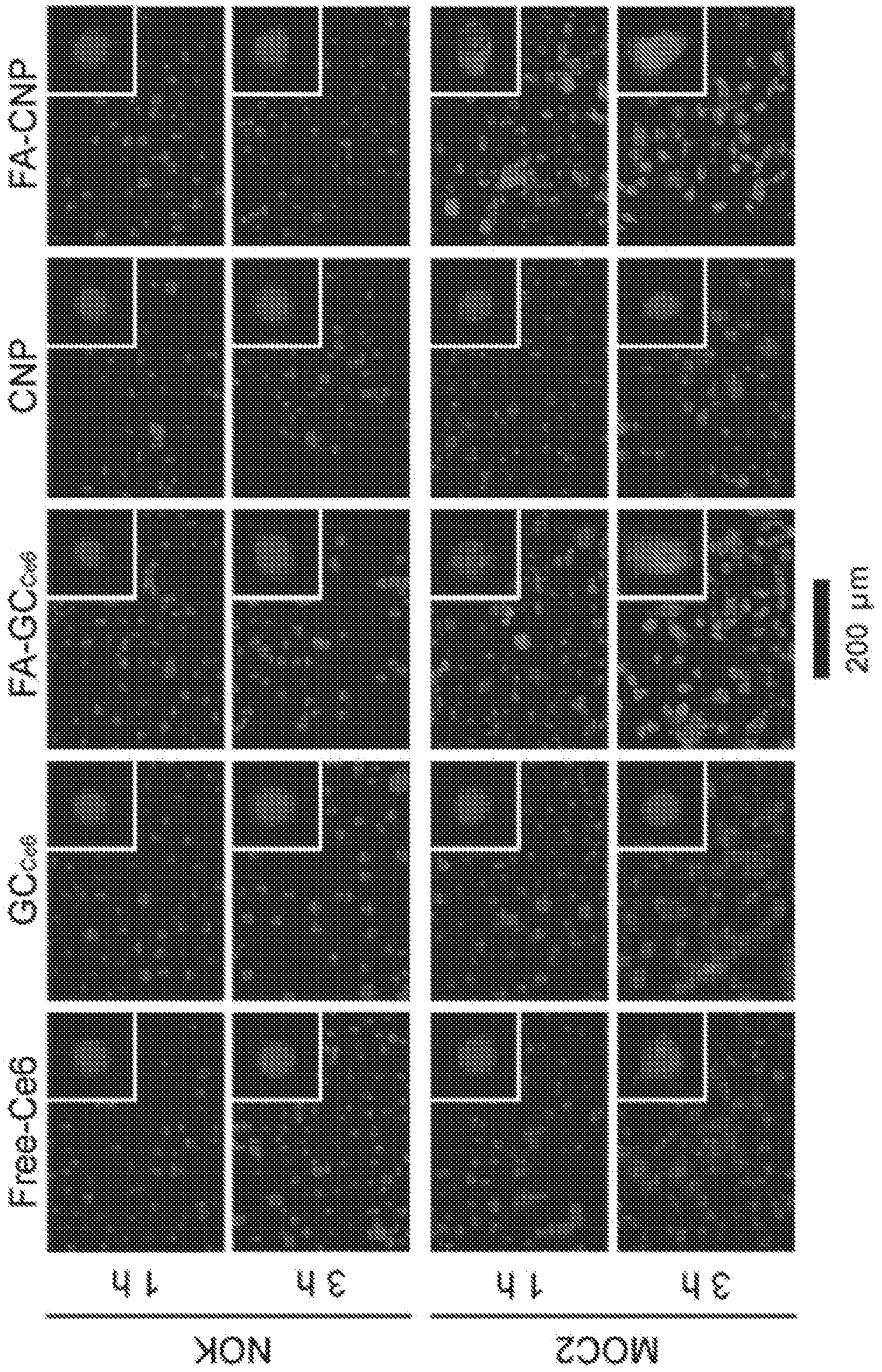

FIGS. 14A and 14B depict cell viability (FIG. 14A) and cellular uptake (FIG. 14B).

Figure 15A:
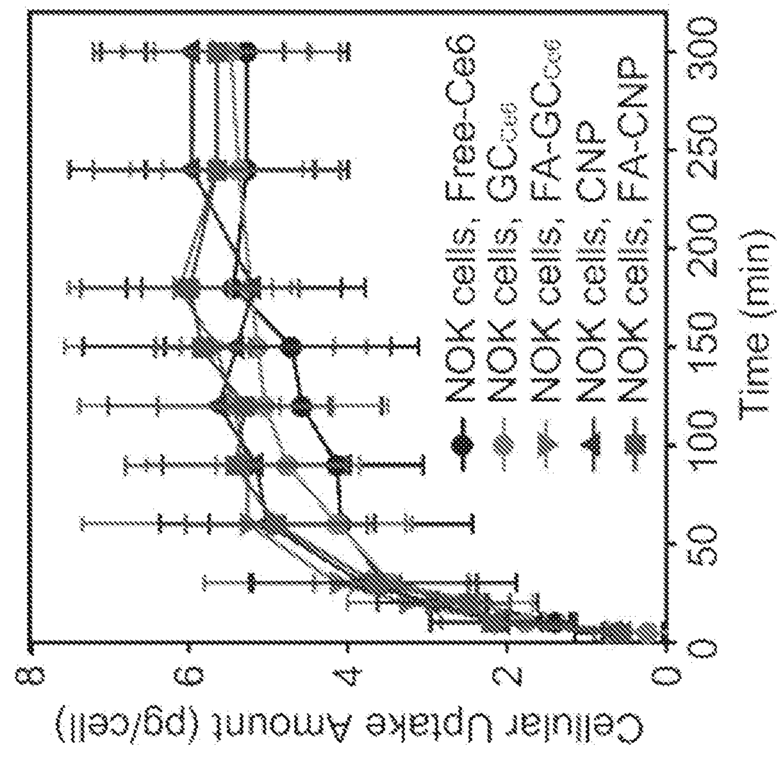
Figure 15B:
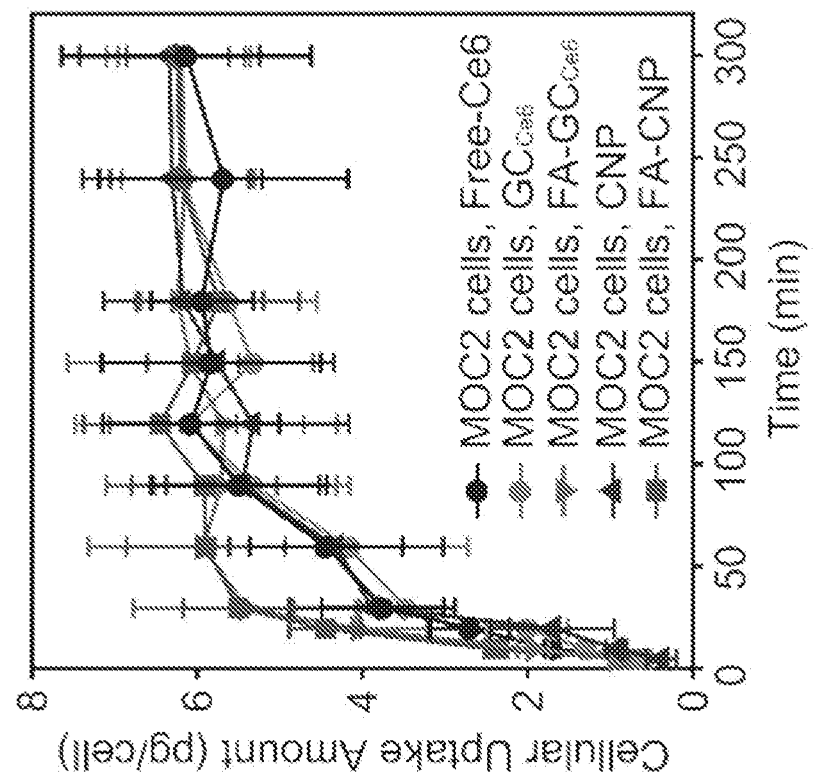

FIGS. 15A and 15B demonstrate cellular uptake of NOK (FIG. 15A) and MOC2 (FIG. 15B) cells treated with respect to time of free-Ce6, GCCe6, FA-GCCe6, CNP and FA-CNP.

Figure 16:
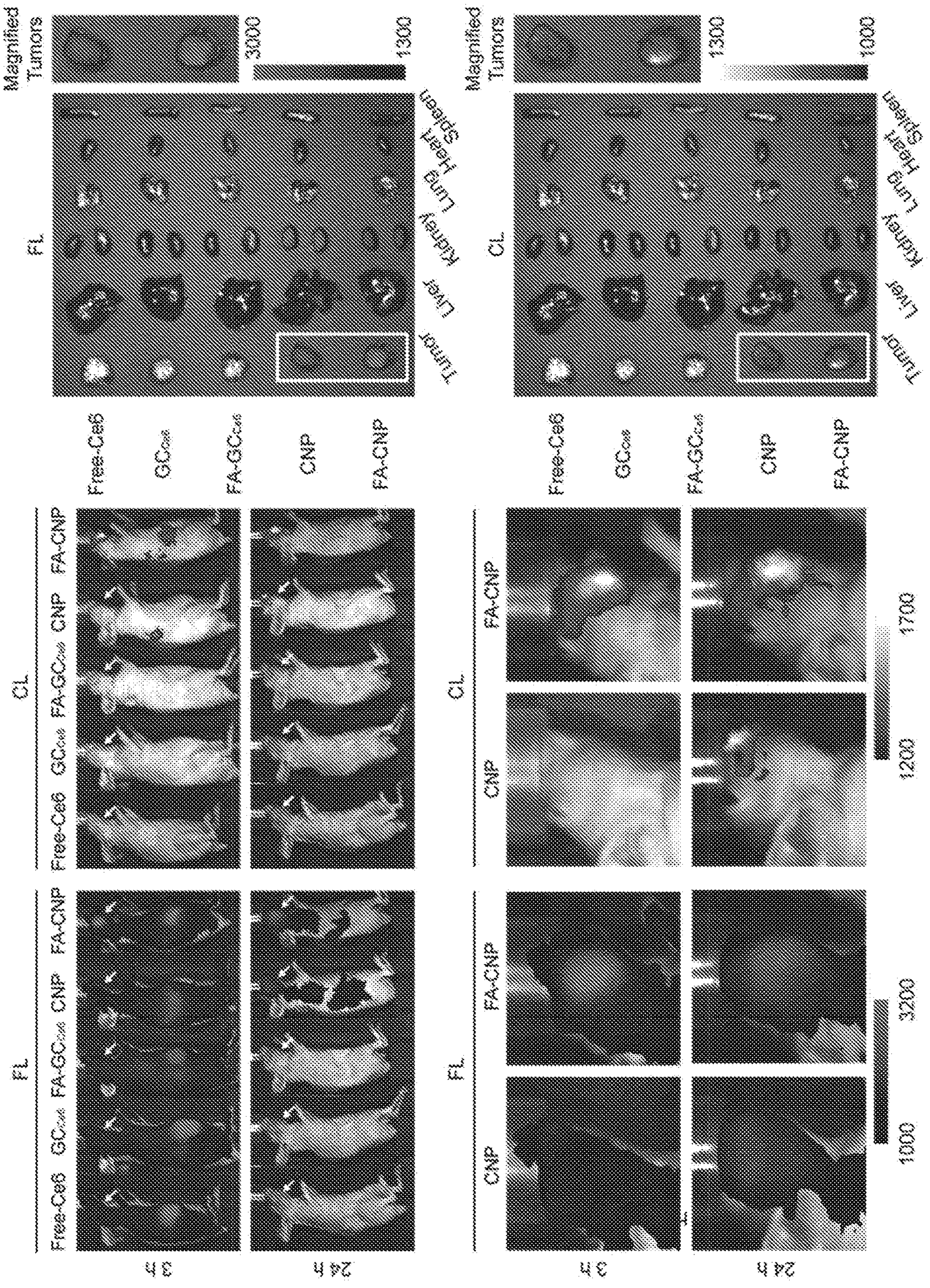

FIG. 16 depicts in vivo imaging validating that the CNPs are efficacious in vivo and label tumors as expected.

Figure 17:
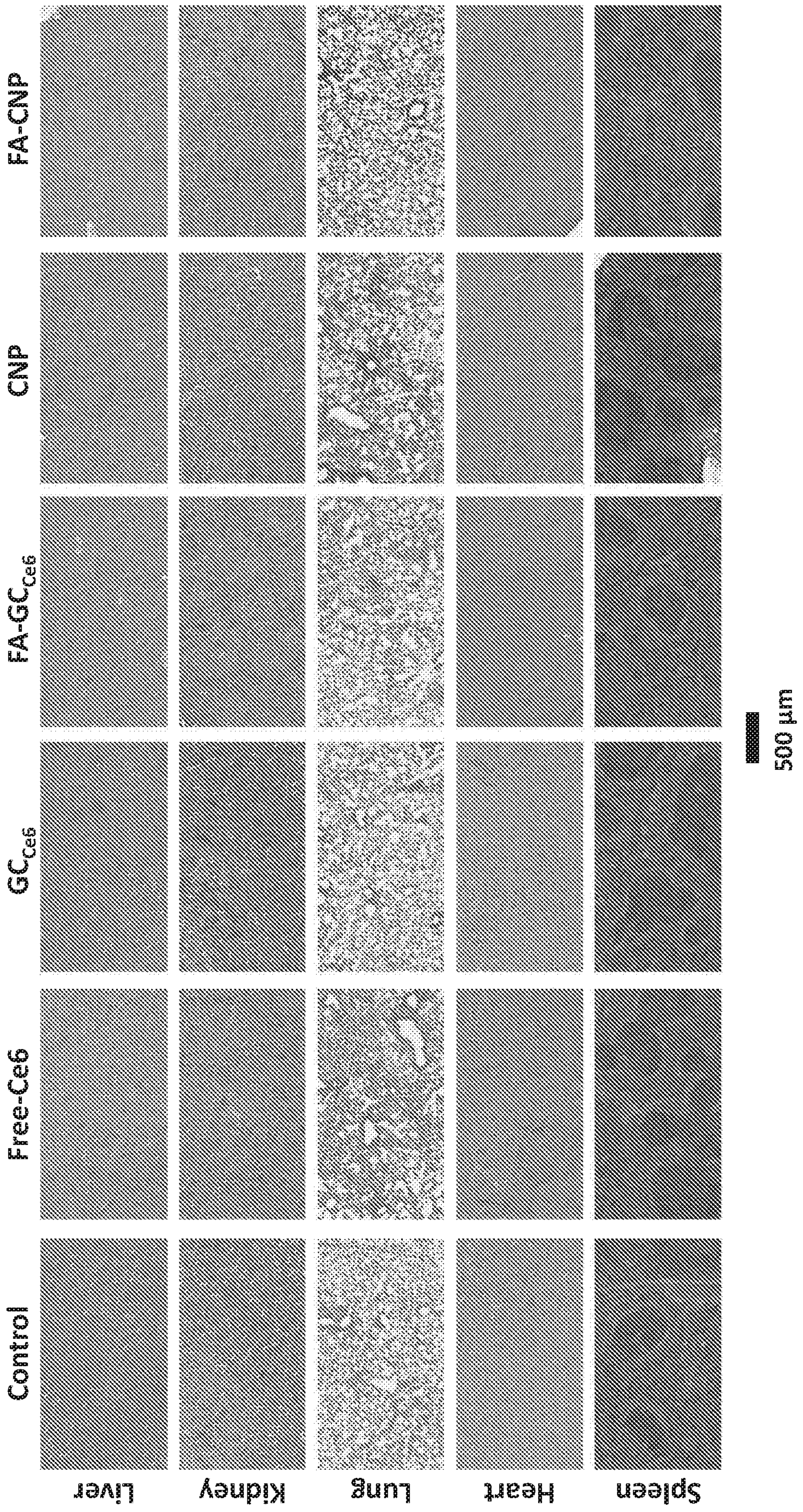

FIG. 17 depicts histology data from spleen, heart, lung, kidney, and liver tissue.

DETAILED DESCRIPTION OF THE INVENTION

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "abnormal" when used in the context of organisms, tissues, cells or components thereof, refers to those organisms, tissues, cells or components thereof that differ in at least one observable or detectable characteristic (e.g., age, treatment, or time of day) from those organisms, tissues, cells or components thereof that display the "normal" (expected) respective characteristic. Characteristics that are normal or expected for one cell or tissue type might be abnormal for a different cell or tissue type.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, a disease or disorder is "alleviated" if the severity of a symptom of the disease or disorder, the frequency with which such a symptom is experienced by a patient, or both, is reduced.

As used herein, the term "effective amount" or "therapeutically effective amount" of a compound is that amount of compound that is sufficient to provide a beneficial effect to the subject to which the compound is administered.

As used herein, the term "effective amount" of a delivery vehicle refers to an amount sufficient of the delivery vehicle to effectively entrap, bind or deliver a compound.

As used herein, the term "electromagnetic radiation" includes radiation of one or more frequencies encompassed within the electromagnetic spectrum. Non-limiting examples of electromagnetic radiation comprise gamma radiation, X-ray radiation, UV radiation, visible radiation, infrared radiation, microwave radiation, radio waves, and electron beam (e-beam) radiation. In one aspect, electromagnetic radiation comprises ultraviolet radiation (wavelength from about 10 nm to about 400 nm), visible radiation (wavelength from about 400 nm to about 750 nm) or infrared radiation (radiation wavelength from about 750 nm to about 300,000 nm). Ultraviolet or UV light as described herein includes UVA light, which generally has wavelengths between about 320 and about 400 nm, UVB light, which generally has wavelengths between about 290 nm and about 320 nm, and UVC light, which generally has wavelengths between about 200 nm and about 290 nm. UV light may include UVA, UVB, or UVC light alone or in combination with other type of UV light. In one embodiment, the UV light source emits light between about 350 nm and about 400 nm. In some embodiments, the UV light source emits light between about 400 nm and about 500 nm.

As used herein, an "instructional material" includes a publication, a recording, a diagram, or any other medium of expression that can be used to communicate the usefulness of a composition or method of the invention in the kit for treating, preventing or alleviating various diseases or disorders recited herein. Optionally, or alternately, the instructional material can describe one or more methods of treating, preventing or alleviating diseases or disorders in a cell or a tissue of a mammal. The instructional material of the kit of the invention can, for example, be affixed to a container that contains the identified composition or delivery system of the invention or be shipped together with a container that contains the identified composition or delivery system. Alternatively, the instructional material can be shipped separately from the container with the intention that the instructional material and the composition be used cooperatively by the recipient.

As used herein, the terms "patient," "subject," "individual" and the like are used interchangeably, and refer to any animal, or cells thereof whether in vitro or in situ, amenable to the methods described herein. A "subject" or "patient," as used therein, may be a human or non-human mammal. Non-human mammals include, for example, livestock and pets, such as ovine, bovine, porcine, canine, feline, and murine mammals. In a non-limiting embodiment, the patient, subject or individual is a human.

As used herein, the term "polymer" refers to a molecule composed of repeating structural units typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "therapeutic" treatment refers to a treatment administered to a subject who exhibits signs of pathology, for the purpose of diminishing or eliminating those signs.

As used herein, the term "treating a disease or disorder" means reducing the frequency with which a symptom of the disease or disorder is experienced by a patient. Disease and disorder are used interchangeably herein.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 and the like, as well as individual numbers within that range, for example, 1, 2, 2.7, 3, 4, 5, 5.3, and 6. This applies regardless of the breadth of the range.

DESCRIPTION

The present invention provides compositions and methods for detecting cancer in a subject. In some embodiments, the cancer includes, for example, prostate cancer, rectum cancer, colon cancer, uterine cancer, pancreatic cancer, lung cancer, and other non-superficial cancers. Embodiments of the present invention provide biocompatible glycol chitosan nanoparticles suitable for dual modality optical imaging. Embodiments of the present invention provide methods for fabricating glycol chitosan nanoparticles. Embodiments of the present invention provide methods for detecting a tissue including cancer tissue in a subject using compositions provided by the present invention.

Glycol Chitosan Nanoparticles

The present invention provides biocompatible dual-modality optical imaging nanoparticles. The nanoparticles of the present invention may include nanoparticles suitable for optical imaging using both fluorescence (FL) and/or luminescence including, for example, chemiluminescence (CL) and/or bioluminescence (BL). That is, the nanoparticles may include nanoparticles conjugated with one or more compounds suitable for optical imaging.

The present invention provides glycol chitosan nanoparticles (CNPs) that are conjugated with one or more compounds that can produce an optical imaging signal. For example, the CNPs may be conjugated with a photosensitizer and a singlet oxygen releasing agent.

The photosensitizer may include one or more of a porphyrin, a chlorin, a dye, and the like. For example, the photosensitizer may include one or more of porphin, protoporphyrin, octaethylpophyrin, tetraphenylporphyrin, aminolevulinic acid, silicon phthalocyanine, temoporfin, chlorin e6, hematoporphyrin, benzoporphyrin, pheophorbide A, one or more bacteriochlorins, isobacteriochlorins, and the like.

The singlet oxygen releasing agent may include an agent that exists in an oxygen-free form and an oxygen-loaded form. The singlet oxygen releasing agent may include, for example, analogues of pyridone, furan, cyclopentadiene, naphthalene, anthracene, etc. That is, in embodiments of the CNPs that include pyridone (i.e., the oxygen-free platform of pyridone-endoperoxide) as the single oxygen releasing agent, the oxygen-free form of the single oxygen releasing agent may include pyridone. In embodiments of the CNPs that include pyridone-endoperoxide as the singlet oxygen releasing agent, the oxygen-loaded form of the singlet oxygen releasing agent may include pyridone-endoperoxide. The singlet oxygen releasing agent in its oxygen-free form (i.e., pyridone) can react with oxygen under irradiation to form the singlet oxygen releasing agent in its oxygen-loaded form (i.e., pyridone-endoperoxide). The oxygen-loaded singlet oxygen releasing agent in its oxygen-loaded form can decompose to form: 1) singlet oxygen and 2) the singlet oxygen releasing agent in its oxygen-free form, (i.e., pyridone).

Embodiments of the CNPs of the present invention include CNPs, which, when excited, emit fluorescence in the near-infrared range of the electromagnetic spectrum. That is, the CNPs may have an emission maxima between about 650 nm and about 900 nm.

Embodiments of the CNPs may have an emission maxima of about 670 nm. Embodiments of the CNPs may be conjugated with fluorophores that have a near-infrared fluorescence emission maxima, including for example, porphyrins (e.g., chlorin e6), cyanines (e.g. Cy5.5, Cy7, ICG, PPCy), rhodamines, squaraines, phthalocyanines, BODIPY, and the like.

Embodiments of the CNPs of the present invention include CNPs, which, when activated, emit luminescence (i.e., chemiluminescence). The CNPs include CNPs that emit luminescence without requiring an external substrate. That is, the CNPs of the present invention may include CNPs that emit auto-luminescence. The CNPs may emit auto-luminescence when the singlet oxygen releasing agents release singlet oxygens, which can then activate the one or more photosensitizer compounds (i.e., are NIR fluorophores as well), thereby generating a luminescence signal. The CNPs may generate an NIR chemiluminescence emission signal (i.e., luminescence by chemical reactions) with a high signal-to-noise ratio (SNR) of up to about 20 in a 2.5-cm target tissue. In some embodiments, a greater SNR may be achieved when the target tissue includes a deeper tissue. The CNPs may have a light penetration depth of up to about 4 cm into a target tissue. That is, the CNPs may generate a chemiluminescence signal that is detectable up to 4 cm deep into a target tissue. At the light penetration depth, the generated chemiluminescence signal may have a high SNR. In some embodiments, the chemiluminescence signal has a light penetration with a high SNR at a depth at which the fluorescence signal has a negligible SNR. The generated chemiluminescence signal may have light penetration detectable at a depth greater than 4 cm into a target. The chemiluminescent signal may have a light penetration depth of about 1 cm to about 4 cm, about 4 cm to about 7 cm, about 7 cm to about 10 cm, and the like. The fluorescence signal may have a light penetration depth of about 1 mm to about 5 mm, about 5 mm to about 10 mm and the like.

Embodiments of the CNPs include glycol chitosan nanoparticles having a diameter of about 200 nm to 400 nm. The CNPs of the present invention may have a diameter of below 200 nm. For example, the CNPs may have a diameter of about 50 nm to about 200 nm. Embodiments of the CNPs of the present invention may include CNPs constructed from depolymerized chitosan. CNPs constructed from depolymerized chitosan include CNPs that may have a diameter of less than about 200 nm. CNPs constructed from depolymerized chitosan may have a diameter of up to about 25 nm, about 50 nm, about 75 nm, about 100 nm about 125 nm, about 150 nm, about 175 nm, about 200 nm, and the like.

Functionalized CNPs

Embodiments of nanoparticles of the present invention include glycol chitosan nanoparticles (CNPs) that may be further conjugated with one or more compounds to improve CNP biocompatibility. For example, the CNPs may be further conjugated with one or more compounds including, for example, polyethylene glycol (PEG).

Embodiments of the nanoparticles of the present invention may further include CNPs that are conjugated with functionalized PEG. The PEG may be functionalized with one or more compounds including, for example one or more small molecule targeting ligands. The one or more small molecule targeting ligand may include one or more ligands including, for example, folate, PSMAi, bis-Zn-DPA, and the like. That is, the CNPs may be conjugated with one or more of folate-polyethylene glycol (PEG), PSMAi-PEG, bis-Zn-DPA-PEG, and the like.

Methods of Fabricating Glycol Chitosan Nanoparticles

Embodiments of the present invention provide methods 700 for fabricating glycol chitosan nanoparticles.

Referring now to FIG. 7, step S701 of method 700 may include reacting chlorin e6 (Ce6) and glycol chitosan under suitable conditions that allow for coupling of Ce6 to glycol chitosan. In some embodiments, chlorin e6 is dissolved in a buffer including for example, a 2-(N-morpholino)ethanesulfonic acid (MES) buffer. The chlorin e6 may be prepared at a concentration of about 5-10 mol %. The buffer may also include 1-ethyl-3-(3-dimethylaminopropyl)carbodiimide hydrochloride (EDC) and N-hydroxysuccinimide (NHS). The chlorin e6, EDC, and NHS may be combined in the MES buffer thereby forming a mixture. The mixture may be mixed using suitable means including for example, stirring, for a suitable duration of time including, for example, about 2 hours. The mixture of chlorin e6, EDC, and NHS may be combined with glycol chitosan. In certain embodiments, the chitosan-containing mixture is pH-adjusted to a suitable pH including, for example pH 8. In certain embodiments, the chitosan-containing mixture is stirred for a suitable duration including, for example, up to about 24 hours.

Embodiments of step S702 may include reacting the glycol chitosan with one or more small molecule ligands, as described herein, under suitable reaction conditions to allow one or more small molecule ligands may be prepared at a concentration of about 5-10 mol %.

Embodiments of step S703 of method 700 may include reacting a derivatized singlet oxygen releasing agent with the Ce6-coupled glycol chitosan under conditions that allow for coupling of the derivatized singlet oxygen releasing agent to the Ce6-coupled glycol chitosan. For example, activated pyridone-COOH in combination with EDC and NHS may be combined with the glycol chitosan mixture in a suitable manner. The combined mixture may be pH adjusted to a suitable pH including for example, a pH of 8. The combined mixture may be incubated for a suitable duration of time including for example overnight.

Embodiments of step S704 of method 700 may include isolating the resulting glycol chitosan nanoparticles that have been coupled to Ce6 and derivatized singlet oxygen releasing agent. The resulting coupled chitosan nanoparticles conjugated with Ce6 and derivatized singlet oxygen releasing agent may be isolated from uncoupled nanoparticles may be isolated using any suitable means, including, for example, dialysis. In some embodiments, the isolated coupled nanoparticles may be collected and lyophilized. The lyophilized coupled nanoparticles may be redissolved in an appropriate buffer solution including, for example a phosphate buffer saline solution (PBS).

Embodiments of step S705 of method 700 may include irradiating the coupled chitosan nanoparticles that may be dissolved in an appropriate buffer such as PBS. The coupled chitosan nanoparticles may be irradiated using suitable means including, for example, using a halogen lamp. The coupled chitosan nanoparticles may be irradiated in the presence of oxygen bubbling in order to oxygen-load the singlet oxygen releasing agent. The derivatized singlet oxygen releasing agent may include one or more pyridone derivatives, including, for example, one or more pyridone derivatives as described herein. The oxygen-loaded singlet oxygen releasing agent may include, for example, one or more pyridone endoperoxide derivatives as described herein.

One or more steps of method 700 may be implemented, in some embodiments, to form compositions as described herein. Although method 700 is depicted as discrete blocks, various blocks may be divided into additional blocks, combined into fewer blocks, or eliminated, depending on the desired implementation.

Methods for Detecting a Target Tissue

Embodiments of the present invention provide method 800 for detecting a target tissue in a subject. The target tissue may include any tissue including, for example, a tumor including, for example, a prostate tumor. The target may include other target tissue that may have a distinct phenotype. The subject may include any subject in need thereof, including for example a mammalian subject such as a human.

Embodiments of step S801 of method 800 may include administering to a subject an effective amount of CNPs of the present invention, as described herein. The CNPs may include oxygen-loaded CNPs. The effective amount may include any suitable amount of CNPs so that targeted tissue is detectable. That is, a suitable amount of CNPs are administered so that CNPs located in, on, near or within a targeted tissue emit a signal that reaches and/or exceeds a detection threshold relative to a comparator control. The effective amount may further include any suitable amount so that targeted tissue can be distinguished from non-targeted tissue. The CNPs may be administered using any suitable route, including for example intravenously, intraperitoneally, intramuscularly, and the like.

Embodiments of step S802 of the method 800 may include imaging the subject using an optical imaging detection modality. The subject may be imaged using an imaging system (e.g., Perkin Elmer™ IVIS® Lumina in vivo imaging system, Perkin Elmer™ IVIS® Spectrum in vivo imaging system, and the like) that may include one or more cameras suitable for detecting an optical signal. For example, the imaging system may include one or more cameras suitable for imaging a fluorescence signal, a luminescence signal, and/or combinations thereof. The luminescence signal may include chemiluminescence, bioluminescence, Cherenkov luminescence, and the like.

Embodiments of step S803 of method 800 may include detecting a signal in the subject. For example, step S803 may include detecting the presence or absence of a signal relative to a comparator control, wherein the presence of a signal indicates a positive signal. Step S803 may include detecting a tissue of interest in a subject. That is, the presence of a signal may be detected in a tissue of interest relative to a comparator control, thereby detecting the target tissue of interest.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Fabrication and Validation of Dual-Modality Optical Imaging Probes The widespread introduction of planar optical imaging stations has enabled incorporation of small animal optical imaging into mainstream biomedical research. These techniques are already close to clinical application. Optical imaging is amenable to high throughput studies, because the images can be acquired in a few seconds and multiple subjects can be simultaneously imaged. In contrast to other molecular imaging methods such as X-ray, MRI, PET, SPECT, and so forth, optical imaging shows is highly sensitive, cost efficient, and straight forward to use. However, it has an obvious limitation for in vivo imaging because of its short penetration depth (1-20 mm), caused by the light scattering by blood tissues and other biological components—this restricts use of the current methods for in vivo optical imaging in the clinic.

The objective of the current research is to fabricate near-infrared chemiluminescent and fluorescent biocompatible nanoparticles for dual modality optical imaging of early stage cancer. The chemiluminescence is thermally-activated at body temperature, and the nanoparticles can be stored at low temperature (<−20° C.). The present results in mice reveal that chemiluminescence imaging permits identification of target sites that are about 4 cm below the body surface, which is about several times deeper than is currently achieved using planar fluorescence imaging. The research is expected to significantly advance the use of in vivo optical imaging for the early diagnoses of tumors located at relatively deep sites, and leads to the development of associated protocols for clinical use in humans.

Here, practically useful NIR chemiluminescent (CL) probes have been developed, which can penetrate deeper tissues (>4 cm), for rapid and non-invasive imaging of PCa at early stages. The method developed herein is easy to implement, and facilitates early diagnosis of tumors that are located relatively deep within tissues. Furthermore, this method helps to guide transrectal sampling with improved detection rate and can be combined with an intraoperative optical imaging device to provide a sensitive and real-time solution to reduce the risk of positive margins.

Methods

Fabrication of CFL CNPs

Figure 1A:
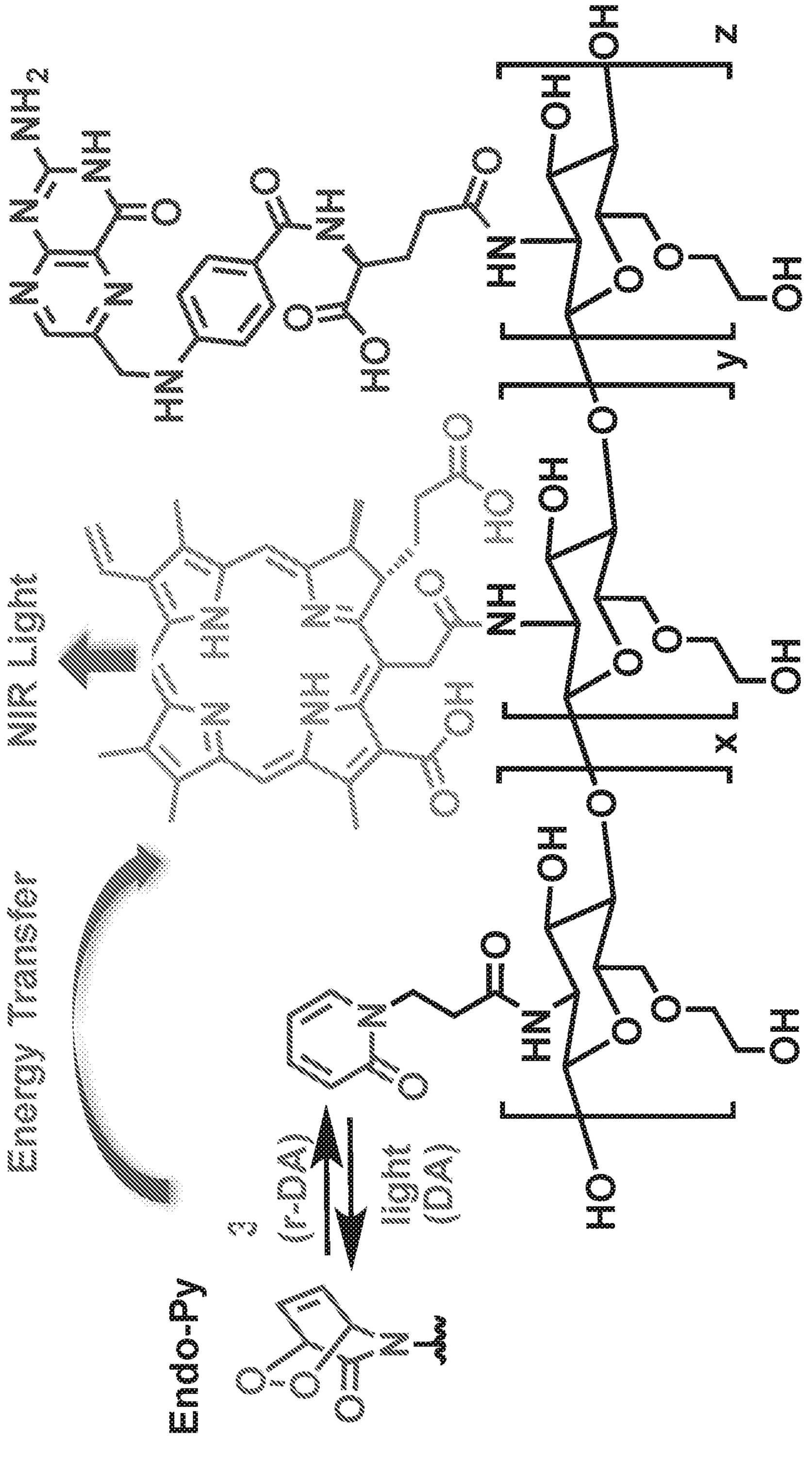
FIG. 1A depicts the chemical structure of the glycol chitosan-based nanoparticle (CNP) and illustrates energy transfer from singlet oxygen ($^1O_2$) to chlorin e6 (Ce6) when the CNP warmed to 37° C. to emit near-infrared (NIR) light.
Figure 1B:
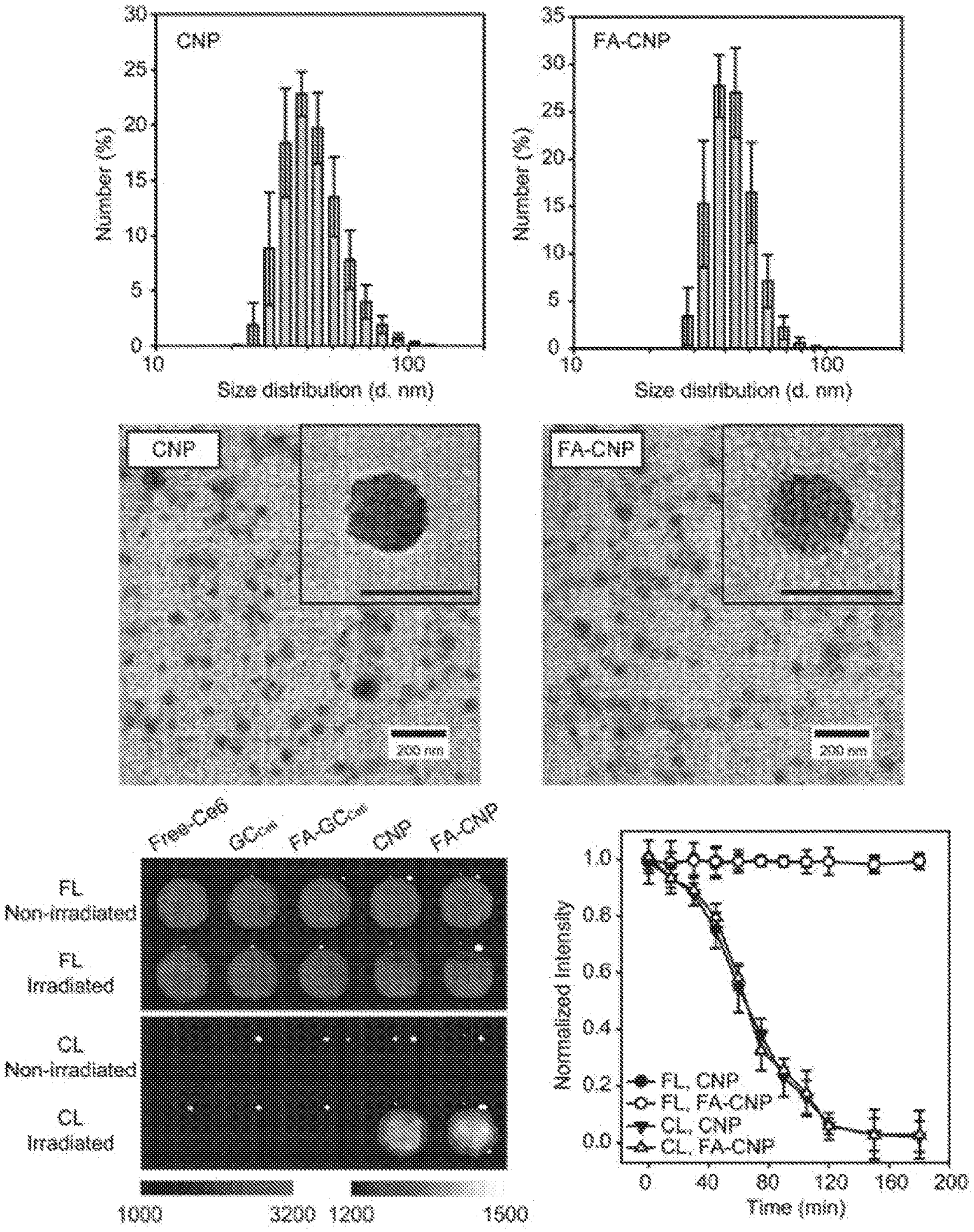
FIG. 1B depicts Dynamic Light Scattering (DLS) and Scanning Electron Microscope (SEM) images of the CNPs (scale bar=500 nm).

Biocompatible and biodegradable glycol chitosan (CS) NPs (CNPs) have been successfully fabricated herein. The CNP consists of pyridone and chlorin e6 (the ratio of Py to Ce6 is 25:1) and under irradiation of light, the pyridone undergoes 4+2 cycloaddition (Diels-alder reaction) to afford the pyridone endoperoxide with 102 that is generated by the Chlorin e6 in PBS. Then, the pyridone endoperoxide decomposes thermally into the parent pyridone, while extruding $^1O_2$ (shown in FIG. 1A). This cycloreversion reaction (retro Diels-Alder reaction) exhibits NIR CL due to the transfer of energy from $^1O_2$ (94 $kJ \cdot mol^{-1}$) to Ce6. It can be stored indefinitely at −20° C. and when warmed to body temperature, Py-EP undergoes a unimolecular cycloreversion reaction that releases $^1O_2$ and emits NIR light. Ce6 is a promising NIR fluorophore (λem=670 nm in PBS) as well as a photosensitizer, because it has a high sensitizing efficacy and is rapidly eliminated from the body and Py is a platform of pyridone-endoperoxide (Py-EP), a singlet oxygen release agent. The fabrication of CNPs is technically straightforward: 1) Ce6 (5 mol % of the amines on CS), 1-ethyl-3-(3-dimethylaminopropyl)carbodiimide hydrochloride (EDC), and N-hydroxysuccinimide (NHS) were dissolved/stirred in MES buffer for 2 hours to activate the carboxylic acids on Ce6; 2) The mixture was added into a solution of CS (MW=120 kDa, 1 g in PBS), which was then adjusted to pH 8, and the solution was vigorously stirred for 24 hours at room temperature; 3) Activated 3-(2-oxo-1,2-dihydropyridin-1-yl)propanoic acid (Py-COOH, 120 mol %) with EDC and NHS in MES buffer was added into the CS solution, and it was adjusted to pH 8; 4) After 24 hours, the resultant solution was dialyzed against deionized water for 3 days using a dialysis membrane (MWCO: 12-14 kDa) to remove unreacted Ce6 and other components; 5) The CS conjugates were collected and lyophilized. 6) the CS conjugate powders were re-dissolved in PBS (pH 7.4), and sonicated three times (for 2 minutes) using a probe-type sonicator. The produced CNPs were well dispersed in PBS. Scanning Electron Microscope (SEM) and Dynamic Light Scattering (DLS) images of the CNPs reveal clusters of NPs with sizes ranging from 200 nm to 400 nm (FIG. 1B).

To optimize size distribution of the CNP for improving the EPR effect, glycol chitosan (GC) was depolymerized to decrease its Mw, as follows 1:1) GC (2.0 g) was dissolved in hydrochloric acid (4 M, 150 mL) and stirred for 3 days at 50° C.; and 2) the depolymerized GC was dialyzed for 2 days against distilled water (MWCO=12-14 kDa) and then freeze-dried. Subsequently, CNPs was fabricated with use of this depolymerized GC 2,3: (i) Ce6 (260 mg, 440 μmol-5 mol % of the amines on the GC), 1-ethyl-3-(3-dimethylaminopropyl)carbodiimide hydrochloride (EDC, 440 mg, 2.3 mmol), and N-hydroxysuccinimide (NHS, 1.1 g, 2.3 mmol) were dissolved/stirred in DMSO (10 mL) to activate the carboxylic acids on Ce6; (ii) the mixture was added into a solution of the depolymerized GC (1.0 g, 12 μmol) in PBS and the solution was vigorously stirred for 24 hours at room temperature; (iii) activated 3-(2-oxo-1,2-dihydropyridin-1-yl)propanoic acid (Py-COOH, 1.7 g, 10 mmol, 120 mol %) with EDC (7.6 g, 40 mmol) and NHS (9.1 g, 40 mmol) in DMSO was added into the GC solution; (iv) after 24 hours, the resultant solution was dialyzed against deionized water for 3 days, using a dialysis membrane (MWCO: 12-14 kDa) to remove unreacted components; (v) the GC conjugates were collected and lyophilized; and (vi) the GC conjugate powders were re-dissolved in PBS (pH 7.4), and sonicated three times (for 2 mins each), using a probe-type sonicator. To obtain FA-conjugated CNP, activated folic acid (190 mg, 440 μmol-5 mol % of the amines on the GC) with EDC (440 mg, 2.3 mmol) and NHS (1.1 g, 2.3 mmol) in DMSO was added into the GC solution prior to (iii). Folate target ligands were successfully conjugated on CNP. The conjugation of FA on CNP was confirmed by UV/Vis spectrophotometer. Free FA exhibits an absorbance at 290 nm and FA-CNP shows significantly high absorbance around 300 nm, whereas the non-coated CNP has similar absorbance with free-Ce6 (FIGS. 1A-1B and FIG. 10). The produced CNPs were well dispersed in PBS, and have a particle size of 50 nm; Dynamic Light Scattering (DLS) and Transmission Electron Microscopy (TEM) images reveal clusters of CNPs with sizes ranging from 30 nm to 100 nm (FIG. 1B).

Characterization of CNP

The cellular uptake of the CNP with different sizes was evaluated and results are shown in FIGS. 9A-9C. The CNP with different sizes were prepared by GC degradation methods. GC is a main component of CNP and its molecular weight has a big influence on particle's diameter. 1,4,5 The effect of size of the CNP on the amount of cellular uptake was evaluated by incubation with MOC2 cells. The CNP with an average size of 49 nm (Sample 1) had a higher amount of cellular uptake compared to the CNP with larger sizes.

Generation of Py-EP (a Singlet Oxygen Release Agent)

CNPs in PBS were irradiated under a halogen lamp (LZC-UVA-01, 235-850 nm), with oxygen bubbling for 60 min to generate Py-EP (FIG. 1A). Preliminary solution state studies reveal that the presence of 20 molar equivalents of Py-EP to Ce6 increases the persistence time, for easy detection of CL for several hours at 37° C. Results from these studies are shown in FIG. 11, and were conducted using 1 to 50 molar equivalents. Once activated, CNPs can be stored for weeks at −20° C., then used as needed.

Results

Optimization of Conjugation Ratio Between Ce6 and Py

Chlorin e6 (Ce6) was used for nanoparticle synthesis because it emits in the NIR region and generates singlet oxygen upon illumination. When the endoperoxide reverts back to pyridone and releases singlet oxygen species, the high energy of singlet oxygen can transfer into the Ce6 to emit NIR light as CL. Initial studies of CL with Ce6 and endoperoxide in solution ensure that the cycloreversion of endoperoxide and release of singlet oxygen successfully provide the activation energy for Ce6, shown in FIGS. 11A-11E. For the optimization, various ratios of Ce6 to endoperoxide were prepared and CL from the samples was measured by an IVIS-Lumina. As soon as the chamber had reached 37° C., CL was detected in dark conditions. The Cy 5.5 filter (635-736 nm) is the most optimal for detecting emission since Ce6 emits NIR wavelengths. The ratio of 1:25 Ce6:endoperoxide showed the maximum CL while the controls with only Ce6 or only endoperoxide did not show any CL. This ratio was further used to determine animal tissue penetration.

Serum Stability

The surface morphologies of the CNP and FA-CNP were characterized using a transmission electron microscopy (TEM, Hitach H7600, Hitachi, Tokyo, Japan). The size distributions of the CNP and FA-CNP were determined with Zetasizer (Nano-S90, Malvern Instruments Ltd, Grovewood, Worcestershire, UK). Each conjugation was confirmed via UV/Vis spectrophotometry (Lambda 35, Perkin Elmer, Norwalk, Conn., USA). To evaluate the colloidal stability in serum, the size of the CNP and FA-CNP in PBS (pH 7.4) containing 20% fetal bovine serum were evaluated for 14 days. As shown in FIG. 12, the CNP was stable in BSA solution retaining their intensity up to 14 days at 37° C. The CNP exhibited high stability in the presence of BSA solution due to the hydrophobic interaction in the core of the CNP. Furthermore, the CNP contains aromatic groups (e.g., Py and Ce6) that can form π-π stacking interaction in addition to hydrophobic interactions. These interactions contribute to the higher formulation stability of the CNP (note that all components in the CNP are covalently conjugated and therefore, the associated side effects caused by release of chemicals from the CNP will be limited).

Cytotoxicity of CNPs on HUVEC

Figure 2:
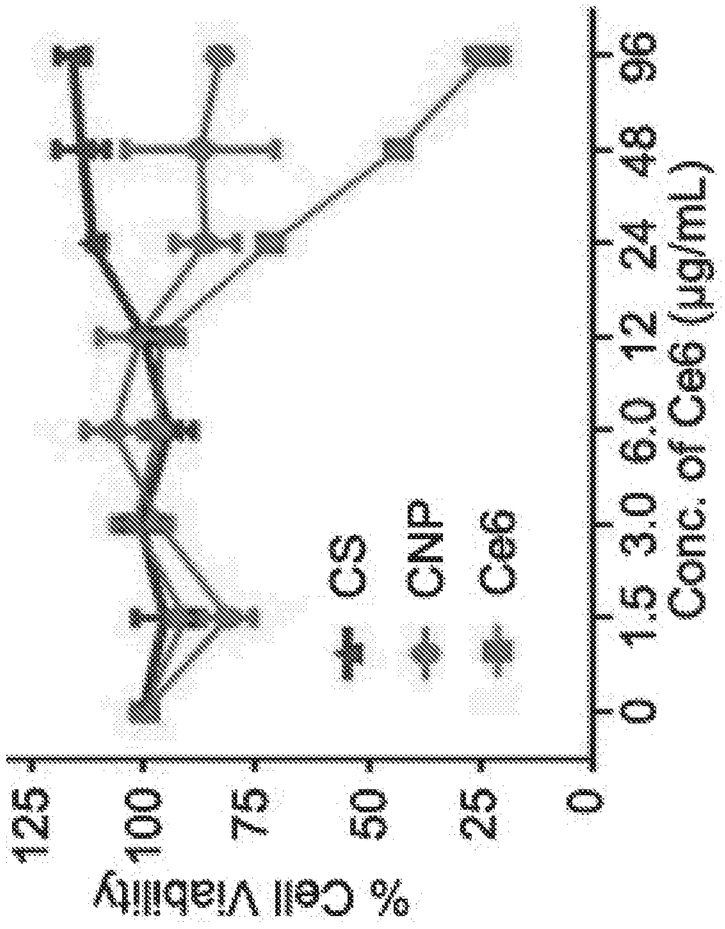
FIG. 2 depicts a graph illustrating cytotoxicity of Ce6, Chitosan (CS), and CNP on human umbilical vein endothelial cells (HUVEC) for 24-hour treatment.

Cytotoxicity assay after treating Human Umbilical Vein Endothelial Cells (HUVEC) for 24 hours with various concentration of Ce6 and its equivalent concentration of CNP shows significant difference in level of toxicity by the MTT assay (FIG. 2). Cell viability was generally not affected by CS and CNP at concentrations lower than 12 μg/mL of Ce6; this is 130 μg/mL of CS or CNP.

In Vivo Optical Imaging of CNPs (Phantom Experiment)

Figure 3A:
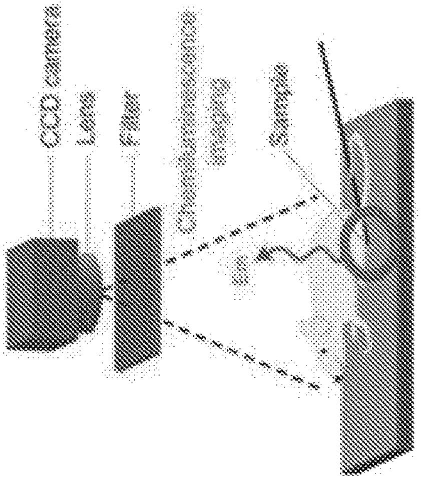
FIGS. 3A-3D depict results demonstrating that chemiluminescence (CL) from CNPs at 37° C. penetrates through a living nude mouse and pork tissues (>4 cm).
Figure 3B:
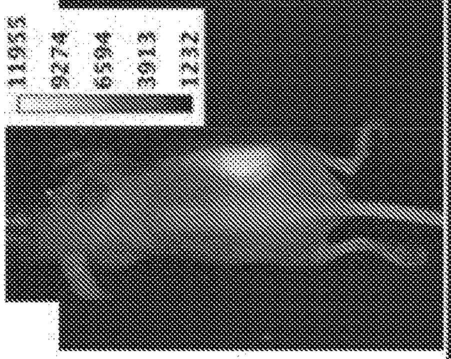
Figure 3C:
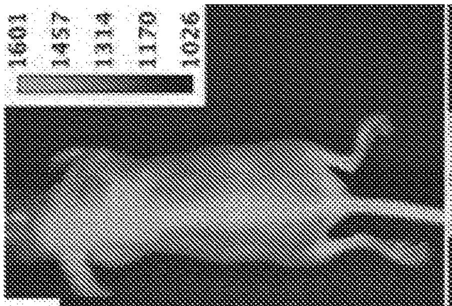
Figure 3D:
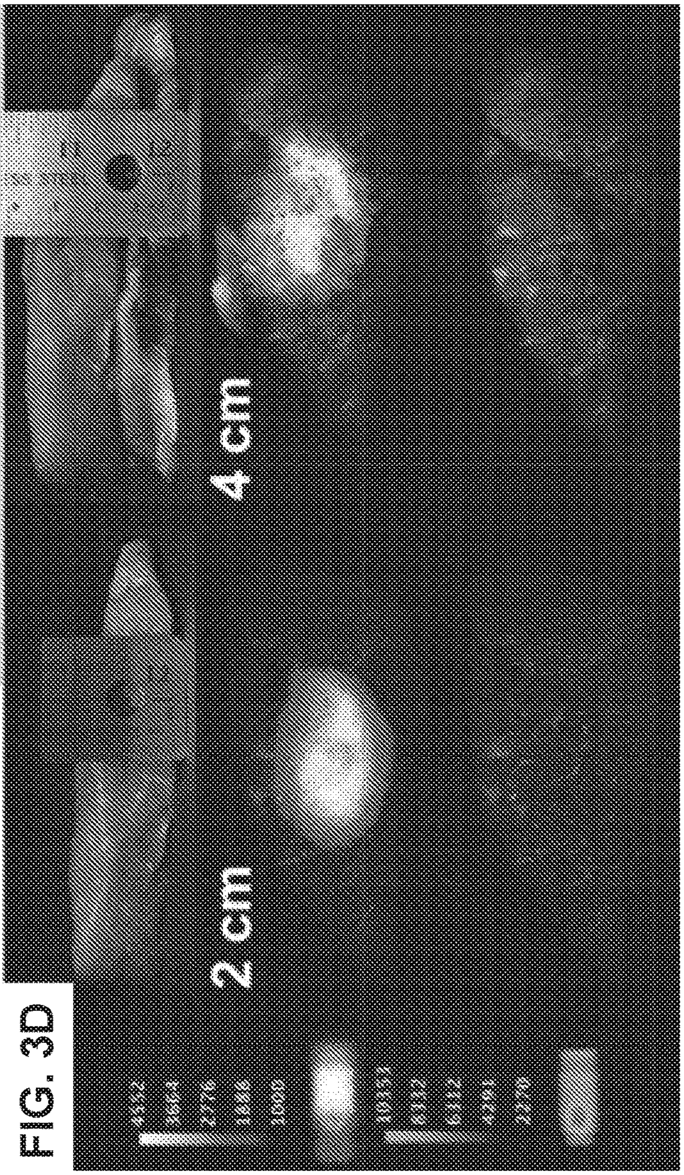

The planar optical images in FIGS. 3A-3D clearly demonstrate the advantage of using CL, which significantly increases tissue penetration as well as the signal-to-noise ratio (SNR), while FL is diminished. The image FIG. 3B shows that NIR CL from a small tube containing a solution of CNPs passes through a living nude mouse that is positioned between the tube and the CCD camera (FIG. 3A). In FIG. 3B and FIG. 3C, the SNR for the transmitted light in the CL mode is an impressive 21 at NIR wavelengths, while the FL mode depicts reflected FL images of the same experimental arrangement plus excitation light; the SNR for FL is 1, and FL from the target site cannot be readily distinguished from the background which is produced by scattering of the excitation light and from tissue autofluorescence. Subsequently, increasingly thick pieces of pork tissue were placed on top of the sample (6 μg/mL of Ce6) (FIG. 3D) and the results show that NIR FL is close to the background noise at the thickness of 2 cm and 4 cm, whereas NIR CL maintains strong intensity up to 4 cm because tissue autofluorescence was eliminated in the absence of real-time excitation. Taken together, these results point to a new paradigm for in vivo optical imaging using this dual modality molecular imaging probe. The NIR CFL CNPs can be imaged first in high contrast CL mode to locate relatively deep anatomical locations in vivo and then subsequently can be implemented in the FL mode to identify microscopic targets in thin histopathology sections taken from the same specimen.

Effect of CNP Size on Functionality

The size of therapeutic NPs for maximally employing the enhanced permeability and retention (EPR) effect is in the range of 50-150 nm. A commercially available CS was used, which has a particle size of 300 nm (average molecular weight (Mw) is 120 kD). This large size would normally have a low efficacy of tumor-targeting, but the EPR effect is enhanced by depolymerizing the CS to decrease its MW, as follows: (i) CS is dissolved in acetic acid (2% w/v) and stirred for 1 hour with $NaNO_2$ (10 mg/mL in water); (ii) the depolymerized CS is precipitated by adjusting to pH 9 with 4M NaOH, washed with 70% MeOH, dialyzed for 2 days, and then freeze-dried; and (iii) the MW of CS is determined using MALDI-TOF-MS. Next, CNPs are fabricated with use of this lower MW CS; typically, the MW of CS decreases to 1/10 (e.g., from 213 kDa to 17 kDa), and the size of the CNPs is reduced by more than 50%. Thus the CNP size is decreased to below 150 nm resulting in the improved EPR effect.

TABLE 1

Half-lives of Py-EPs in water at 37° C.

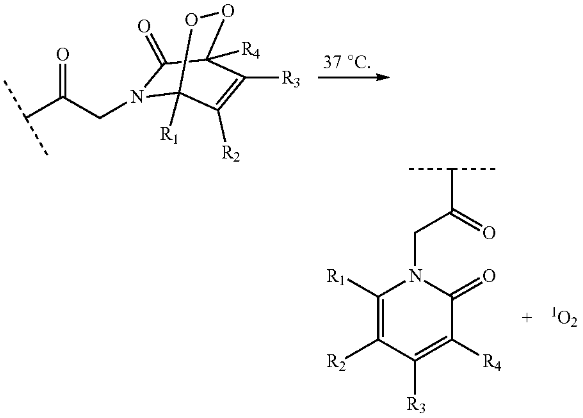

| | $R_1$ | $R_2$ | $R_3$ | $R_4$ | $T_{1/2}$, h (in $H_2O$) |
|---|---|---|---|---|---|
| Py-EP1 | H | H | H | H | 0.5 |
| Py-EP2 | H | H | H | $CH_3$ | 8.5 |
| Py-EP3 | $CH_3$ | H | H | H | 4 |
| Py-EP4 | H | $CH_3$ | H | $CH_3$ | 13 |
| Py-EP5 | $CH_3$ | H | H | $CH_3$ | 4 |
| Py-EP6 | $CH_3$ | $CH_3$ | H | $CH_3$ | 15 |

Various $^1O_2$ Release Agents

The results with the Py-EP, $^1O_2$ release agent show that the half-life of CL is a couple of hours (note that this longer half-life of Py-EP compared with Py-EP1 in Table. 1, that is the same structure, is because Py-EP is inside the hydrophobic core of the CNP)—thus, the lifetime of CL is extended, so it is long enough to target cancers. Other pyridone-derived endoperoxides were designed (Table. 1) that have longer half-lives of cycloreversion (i.e., a longer lifetime of CL). The new designed CNPs within these molecules exhibit CL that is 5-20 times longer than the that of CNPs used in previous results.

CNPs with PEG

To avoid phagocytosis of CNPs, and to enhance their longevity, CNPs are coated with additional PEG (CNPPEG): CNPs are fabricated with Ce6 (5 mol %), PEG-NHS (5 mol %, 2 kDa), and Py (Py 1-6 in Table 1, 90 mol %). This additional coating improves the biocompatibility of the CNPs and reduce the absorption of circulating plasma proteins onto their surface: in particular, it prevents self-aggregation caused by poor functionalization on the NPs. PEG also protects CNPs from being cleared rapidly by the RES, and extends their biodistribution.

Small-Molecule Ligands on CNPs

The use of magnetic NPs (aminated $Fe_3O_4$) modified with bis-Zn-DPA-PEG-COOH has efficacy for clearing bacteria and endotoxin from the blood stream. In order to synthesize bis-DPA-PEG-COOH (note that $Zn^{2+}$ is added into the solution of the CNP coated with bis-DPA-PEG to obtain CNPZn-DPA), the prepared bis-DPA, EDC and NHS are added to and stirred in dry dichloromethane (DCM) for 4 hours at room temperature. The solvent is removed under reduced pressure, and the crude product is purified by flash chromatography to obtain DPA-succinimidyl valerate (DPA-SVA). A mixture of $NH_2$—PEG-COOH (2, 5, or 10 kDa) and DPA-SVA is stirred for 2 hours in DCM with N,N-diisopropylethylamine (DIPEA) and then bis-DPA-PEG-COOH is quantitatively obtained after size exclusion chromatography in chloroform. The synthesis of ligands, folate and PSMAi, as described in FIG. 4, and is used to obtain Folate-PEG-COOH and PSMAi-PEG-COOH with the same procedure as above for further immobilization on the CNPs.

CNPs with bis-DPA-PEG-COOH, Folate-PEG-COOH, or PSMAi-PEG-COOH CNPs are coated with bis-DPA-PEG-COOH ($CNP_{Zn\text{-}DPA}$) through carbodiimide chemistry for its PS-affinity, PS-selectivity, and metabolic stability. CNPs include 5 mol % of Ce6, 5 mol % of bis-Zn-DPA-PEG-COOH ($Zn^{2+}$ is added into the solution of the CNP), and 90 mol % of Py. To evaluate the efficiency of binding of the $CNP_{Zn\text{-}DPA}$, the length of the linkage between CNP and bis-Zn-DPA (e.g., 2, 5 and 10 kDa of PEG) is varied. It is reasoned that increasing the amount of bis-Zn-DPA on the CNPs increases this binding strength, and thus enhances binding efficiency. CNPs are synthesized with a variety of bis-Zn-DPA-PEGs (e.g., 5, 10, and 20 mol %), and their efficiency is evaluated. Similarly, the folate molecule ($CNP_{Folate}$) is conjugated to target the FR and the PSMAi ($CNP_{PSMAi}$), in order to associate with PSMA for targeting PCa.

CFL SPIONs

MRI has excellent anatomical resolution and contrast, and is increasingly being used as a first-choice clinical imaging modality. Superparamagnetic iron oxide nanoparticles (SPIONs) are potent clinically approved MRI contrast agents that cause shortening of transverse (T2) proton relaxation times, thereby resulting in dark negative contrast areas of T2-weighted MR images. All clinically approved SPIO contrast agents are synthesized with use of the one-pot procedure described by Molday & MacKenzie, 1982, J Immunol Methods 52(3):353-67. Key advantages of these agents are their easy and scalable fabrication, and the low cost of polysaccharides that are used for their synthesis. However, SPIONs trigger immune-related adverse effects in patients, are rapidly cleared, and show nonspecific uptake by monocytes and macrophages. These unfavorable pharmacokinetics preclude the use of SPIONs for imaging organs and tissues outside of macrophage-rich organs such as liver and spleen. Recently, cross-linked iron oxide nanoparticles (CLIONs) have been prepared by cross-linking ultrasmall (15-30 nm) monocrystalline SPIO with epichlorohydrin (ECH), in the presence of NaOH. Because of their very low transverse relaxivity rate (R2; ~60 $mM^{-1}s^{-1}$), ultrasmall size, and long-circulating properties, CLIONs have become a popular nanoplatform for imaging applications. But despite the need for ultra-small iron oxides that can efficiently penetrate tissues and evade macrophages, these SPIONs have the drawback that their magnetic contrast properties (relaxivity) are relatively low and their cell uptake is less effective compared to that of larger iron oxides. Thus, there is a need to improve their contrast properties, decrease immune recognition, and enhance circulation time. Practically useful SPIONs as MRI contrast agents were designed and fabricated that are hydrogenated, have high transverse relaxivity rates, and efficiently block immune recognition.

SPIONs are synthesized by a one-pot ammonia precipitation reaction of $Fe^{2+}$ and $Fe^{3+}$, in the presence of nonreduced dextran (15-25 kDa). The synthesized SPIONs are cross-linked with ECH in the presence of NaOH. ECH reacts with sugar hydroxyls (via chloride or epoxide) and leads to etherification and cross-linking (FIG. 5), forming a cross-linked dextran hydrogel. While cross-linking, Ce6 anhydride and Py-NHS (FIG. 5), in a 1:20 ratio, are added into the solution to fabricate CFL SPIONs. SPIO are reacted with ECH at a 30 rpm mixing speed, at 23° C., and in a 10N NaOH solution. Ce6 anhydride and Py-NHS are then added to the solution, and mixed at 1400 rpm at 37° C. Finally, the CFL SPION are formed with a molar transverse relaxivity (R2) of 388 $mM^{-1}s^{-1}$ which is much higher than the values previously reported for smaller SPIONs and commercial iron oxides Feridex and Feraheme (100 and 70 $mM^{-1}s^{-1}$, respectively). Similarly, CFL SPION are coated with bis-Zn-DPA ($SPION_{Zn\text{-}DPA}$), folate molecule ($SPION_{Folate}$), and PSMAi ($SPION_{PSMAi}$), via carbodiimide chemistry.

Tissue Penetration Depth

The planar optical images shown in FIGS. 13A-13D clearly demonstrate the advantage of using CL, which significantly increases tissue penetration as well as SNR, even when the FL is diminished. FIG. 13B shows that the NIR CL from a small tube containing a solution of CNPs passes through a living nude mouse that is positioned between the tube and the CCD camera (FIG. 13A). In FIGS. 13B and 13C, the SNR for the transmitted light in the CL mode is an impressive 21 at NIR wavelengths, while the FL mode depicts reflected FL images of the same experimental arrangement plus excitation light; the SNR for FL is 1, and FL from the target site cannot be readily distinguished from background (produced by scattering of the excitation light) and from tissue autofluorescence. Thick pieces of pork tissue was then placed on top of the sample (6 μg/mL of Ce6) (FIG. 13D): results show that NIR FL is close to background noise at thicknesses of 2 m and 4 cm, whereas NIR CL maintains a strong intensity up to a thickness of 4 cm (Note that to the best of the inventor's knowledge, this is the deepest tissue penetration result in optical imaging), because tissue autofluorescence is eliminated in the absence of real-time excitation. Taken together, these preliminary results point to a new paradigm for in vivo optical imaging, using the CFL molecular imaging probe. First, imaging NIR CFL CNPs in high contrast CL mode will be performed to locate relatively deep anatomical locations in vivo, and then in the FL mode to identify microscopic targets in thin histopathology sections from the same specimen.

Cell Viability and Cellular Uptake

NOK (Normal oral keratinocyte) and MOC2 (immunogenic murine squamous cell carcinoma) were used to evaluate the cytotoxicity. The viability of both cells was determined by a Cell Counting Kit-8 (CCK-8) assay in corresponding culture medium after 24 hour incubation with free-Ce6, $GC_{Ce6}$, FA-$GC_{Ce6}$, CNP and FA-CNP (note that the concentrations of CS polymers and CNPs were adjusted using the absorbance of Ce6 at 554 nm). The CNPs show low cytotoxicity against both cells with the concentrations up to 2 mg/mL of Ce6 (i.e., is equivalent to 20 mg/mL of CNPs, >85% viability): particularly, the CNPs has lower toxicity than free-Ce6 at all concentrations because the CNP strongly retains the Ce6 in the core of the CNP due to hydrophobic and π-π interactions.

The cell internalization of CNPs was characterized by a fluorescence microscopy. As shown in FIGS. 14A and 14B, the CNPs quickly enter into NOK and MOC2 cells. After incubation with CNPs for 30 minutes, most of cells show red fluorescence in the cell and then the fluorescence intensity from the cells was saturated after 1 hour; all Ce6s are covalently conjugated and thus the saturation of fluorescence intensity after 1 hour indicates that the cell uptake of CNPs, not the free Ce6, is the dominant factor of this fluorescence increase. Through the cellular uptake study, it was confirmed that CNPs efficiently enter into the cells within 1 hour.

To evaluate the cellular uptake, NOK (Normal oral keratinocyte) and MOC2 (immunogenic murine squamous cell carcinoma) cells were used as folate receptor alpha (FRα)-negative and -positive cells, respectively (FIGS. 15A and 15B). FIGS. 15A and 15B shows the cellular uptake of NOK (FIG. 15A) and MOC2 (FIG. 15B) cells after 1 and 3 hours of incubation. Irrespective of incubation time, there was no significant difference in uptake amount among free-Ce6, $GC_{Ce6}$, FA-$GC_{Ce6}$, CNP and FA-CNP onto NOK cells, suggesting non-specific cellular uptake. In addition, the uptake amounts of CNP onto NOK and MOC2 cells were not significantly different. However, the uptake amount of FA-$GC_{Ce6}$ and FA-CNP onto MOC2 cells was significantly higher than those in other conditions after 1 hour. These results confirmed the strong cellular affinity of FA-$GC_{Ce6}$ and FA-CNP to tumor cells with many folic acid receptors, indicating a tumor-specific uptake of FA-CNP owing to the presence of FA.

For visualization of the cellular uptake, the NOK and MOC2 cells in each well were treated with free-Ce6, $GC_{Ce6}$, FA-$GC_{Ce6}$, CNP and FA-CNP and then subjected to DAPI staining. As shown in FIG. 15B, uptake amount of FA-$GC_{Ce6}$ and FA-CNP onto MOC2 cells were higher than those in other conditions after 1 hour. The fluorescence images matched to the corresponding data in FIGS. 15A and 15B. The enhancement of the cellular uptake is attributed to the presence of FA facilitating receptor-mediated endocytosis. These results suggest that the employment of FA onto CNP can improve the cellular uptake rate as well as specificity even at an early stage.

In Vivo

FIG. 16 shows a typical whole-body imaging with CL and FL pixel intensity maps of an anesthetized mouse at 3 and 24 hours after tail vein injection of free-Ce6, $GC_{Ce6}$, FA- $GC_{Ce6}$, non-targeted CNP, and FA-CNP (2 mg/mL of Ce6). In the case of FA-CNP (active targeting), there was clear evidence for selective accumulation in HNC after 3 and 24 hours through FL and CL while CNP slowly accumulated in the tumor due to the EPR effect (passive targeting). This clearly indicates FA-CNP is efficiently target the HNC because the inoculated MOC2 cell is (FRα)-positive. More importantly, the CL from HNC exhibited significantly high SNR (16±6.9) at 24 hours post-injection of CNPs compared to those of the FL (1.7±0.16). In case of FA-CNPs, the SNR of CL (29±8.2) determined significantly higher than those in the FL (2.5±0.43). The SNR was calculated as the intensity of tumor area divided by the intensity of liver area.

For the animal model, the Murine B4B8 and LY2 squamous cell carcinoma cells were injected sub-mucosally via the intraoral route into the buccal mucosa at a final concentration of $1.0\times10^{6}$/0.1 mL per animal. After palpable tumors had formed (1 week post-injection), the tumor-bearing nude mice were randomly divided into five groups (n=4 per group). For the planar CL and FL imaging, the polymers and CNPs (100 μL in PBS) were intravenously (i.v.) injected into each mouse through tail vein. Each group of mice was imaged at 24 and 48 h post-injection using the IVIS. After euthanizing all animals with carbon dioxide gas, the livers, kidneys, lungs, hearts, spleens and tumors were extracted and photographed using the IVIS imaging. Both CL and FL signals from the mice were observed selectively in the 695-770 nm emission filter channel (cy5.5). In the cases of $CNP_{PEG}$ and $CNP_{Folate}$, there was clear evidence for selective accumulation in HNC after 24 hours through FL and CL: after 48 hours, the intensity of the CL was diminished as expected but surprisingly, the CL from HNC had exhibited significantly high intensity for 24 hours without background noise (FIG. 16). The mice were then sacrificed after 48 hours and their tissues harvested for ex vivo analysis of probe biodistribution. FL intensity images of the excised tissues confirmed the relatively high tumor selectivity of CNPs. The bar graph in FIG. 16 shows that average tumor targeting with $CNP_{Folate}$ (i.e., active targeting) was 3-fold higher than $CNP_{PEG}$ (i.e., passive targeting) and also much higher than controls (Ce6, Ce6-GC, and Ce6/Py-GC) (note that significant CL intensity from the tumor was observed 48 hours post-injection of CNPs, so it would be long enough to target cancers in patients). In summary, $CNP_{PEG}$ and $CNP_{Folate}$ can selectively accumulate in HN tumors in the xenograft animal model and ex vivo biodistribution suggests that $CNP_{Folate}$ (i.e., active targeting) more efficiently targets the tumor compared with non-targeted $CNP_{PEG}$ (passive targeting).

Five-weeks-old female Nu/nu BALB/c mice were purchased from Charles River. For the tumor bearing animal model, the mice were implanted the MOC2 cells to use Head and neck cancer models. MOC2 cells were grown to 75% confluence and harvested and suspended in serum-free DMEM media. Cell suspension was mixed with equal volumes of Matrigel (10 mg/mL) and injected sub-mucosally via the intraoral route into the buccal mucosa at a final concentration of $1\times10^{6}$/0.1 mL per animal. All mice were inoculated at a single site in the right buccal. The mice bearing tumor tissue were randomly divided into five groups (n=5 per group). Treatments were conducted when tumor size reached approximately 50 $mm^3$ (5-6 day post inoculation). For the FL/CL imaging, the mice were anesthetized with isoflurane (5% v/v and maintained 1.5-2% v/v) by placing the mouse in induction chamber. After anesthetization, free-Ce6, $GC_{Ce6}$, FA-$GC_{Ce6}$, CNP and FA-CNP (i.e., prior to the injections, CNPs were activated under irradiation of light to form Py-EP, 0.1 mL equivalent Ce6 concentration of $1.34\times10^{-5}$ mol/kg body weight) in PBS were injected into mice through a tail vein. At predetermined time points, the entire mouse body was imaged using Xenogen IVIS200 imager (Perkin Elmer, Waltham, Mass., USA) at the CU Cancer Center/Radiology Oncology In vivo Optical Gene Imaging Facility Transgenic Facility. CL images were acquired for 5 min, 8×8 binning, field of view D 13.2 cm, f/stop 1, with open filter. Subsequently, the FL images were also acquired for 0.5 sec, 4×4 binning, field of view D 13.2 cm, f/stop 8 with Cy5.5 filters. IVIS 200 parameters were set using living image 2.6 software. Pixel intensity maps were acquired using Living Image software version: 4.3.1.0.15880, and the data was analyzed using ImageJ software version.

After euthanizing mice with carbon dioxide gas, the internal organs (liver, kidney, spleen, heart, and lung) and tumor tissue were extracted and photographed using IVIS imaging. In addition, tumor tissues were excised from the mice at 2 days post-intravenous injection of free-Ce6, $GC_{Ce6}$, FA-$GC_{Ce6}$, CNP and FA-CNP (0.1 mL equivalent Ce6 concentration of $1.34\times10^{-5}$ mol/kg body weight) fixed with 10% Neutral Buffered Formalin solution, and embedded in paraffin, followed by sectioning. The sliced internal organs (5 μm in thickness) were stained with hematoxylin and eosin (H&E) and observed under an optical microscope. In addition, sliced tumor tissues were determined their FL and CL imaging under a confocal laser scanning microscope (Zeusis Nikon, Tokyo, Japan).

Ex Vivo

The mice were then sacrificed after 48 hours and their tissues harvested for ex vivo analysis of probe biodistribution. FL intensity images of the excised tissues confirmed the relatively high tumor selectivity of CNPs. In summary, CNP and FA-CNP can selectively accumulate in HN tumors in the xenograft animal model and ex vivo biodistribution suggests that FA-CNP (i.e., active targeting) more efficiently targets the tumor compared with non-targeted CNP (passive targeting).

FIG. 16 shows FL and CL images of explanted internal organs (liver, lungs, kidney, heart, and spleen) and tumor tissues after 48 hours. There was no significant difference in FL and CL images among free-Ce6, GCCe6 and FA-GCCe6, groups. The FL of CNP was accumulated in the liver and some of them were observed in the kidney. Only a small amount of CNP was found in tumor tissues. However, the FA-CNP was mainly accumulated in tumor tissues. These results indicated that the FA-CNP exhibited superior properties in terms of reticuloendothelial system (RES) avoidance and tumor-targeting efficiency. The CL of FA-CNP was strongly confirmed in tumor tissues at 48 hours, suggesting capability of tumor specific diagnosis. The variations of normalized FL and CL intensities matched to the corresponding data in explanted internal organ and tumor tissues. The CL of tumor tissues in the FA-CNP group was higher approximately 6.3-folds than other tumor intensities. This result indicates that FA-CNP exhibit superior performance with specific tumor diagnosis and targeting for long term CL.

Histology

FIG. 17 shows the histological internal organs (liver, lungs, kidney, heart, and spleen) images after hematoxylin and eosin (H&E) to confirm the toxicity of free-Ce6, GCCe6, FA-GCCe6, CNP and FA-CNP. H&E stained images showed no significant cellular toxicity in all samples compared to the control (non-treated) group. This result clearly confirmed that the low toxicity of CNP and FA-CNP is a highly stable and feasible contrast for optical imaging.

Statistical Analysis

All experimental data were expressed as mean standard deviation. Statistical analysis was evaluated by analysis of variance (ANOVA). Statistical significance was set at $p<0.05$.

Materials

Glycol chitosan (MW=82 kDa, degree of deacetylation=83%) was purchased from Wako Chemicals USA (Richmond, VA, USA). Hydrochloric acid (HCl) was purchased from VWR Analytical (Radnor, PA, USA), folic acid hydrate (FA) was purchased from Tokyo Chemical Industry (TCI, Tokyo, Japan), dimethyl sulfoxide (DMSO) was obtained from EMD Millipore (Billerica, MA, USA), 1-ethyl-3-(3-dimethylaminopropyl)carbodiimide (EDC) was provided by Oakwood Chemical (Estill, SC, USA), and N-hydroxysuccinimide (NHS) was purchased from Chem-Impex International (Wood Dale, IL, USA). 3-(2-oxo-1,2-dihydropyridin-1-yl)propanoic acid (pyridone) was purchased from Enamine Ltd (Kiev, Ukraine). Chlorin e6 (Ce6) was purchased from Frontier Scientific, Inc. (Newark, DE, USA). The dialysis membrane was purchased from Spectrum Laboratories Inc. (MWCO=12-14 kDa, Rancho Dominguez, CA, USA). For the cell study, phosphate buffered saline (PBS), culture medium, and 4',6-diamidino-2-phenylindole dihydrochloride (DAPI) were purchased from Invitrogen (Grand Island, NY, USA). Normal oral keratinocyte (NOK) cells were grown in defined keratinocyte medium. 15 Immunogenic murine squamous cell carcinoma (MOC2) cells were cultured in Iscove's Modified Dulbecco's Media (IMDM) supplemented with 10% fetal bovine serum (FBS) and 1% Primocin. 10 Cell Counting Kit-8 (CCK-8) was purchased from Dojindo Molecular Technologies, Inc. (Kumamoto, Japan). Matrigel was purchased from BD Biosciences (San Jose, Calif., USA). 10% neutral buffered formalin was purchased from Thermo Fisher Scientific (Kalamazoo, Mich., USA).

ENUMERATED EMBODIMENTS

The following exemplary embodiments are provided, the numbering of which is not to be construed as designating levels of importance.

Embodiment 1 provides a biocompatible dual-modality optical imaging nanoparticle, wherein the nanoparticle comprises chitosan, wherein the chitosan is conjugated with: a photosensitizer, and a singlet oxygen releasing agent, which exists in an oxygen-free form or an oxygen-loaded form.

Embodiment 2 provides the nanoparticle of Embodiment 1, wherein the chitosan comprises glycol chitosan.

Embodiment 3 provides the nanoparticle of any of Embodiments 1-2, wherein the photosensitizer comprises chlorin e6.

Embodiment 4 provides the nanoparticle of any of Embodiments 1-3, wherein the singlet oxygen releasing agent in its oxygen-free form comprises pyridone.

Embodiment 5 provides the nanoparticle of any of Embodiments 1-4, wherein the singlet oxygen releasing agent in its oxygen-loaded form comprises pyridone-endoperoxide.

Embodiment 6 provides the nanoparticle of any of Embodiments 1-5, wherein the singlet oxygen releasing agent in its oxygen-free form can react with oxygen under irradiation to form the singlet oxygen releasing agent in its oxygen-loaded form, which decomposes to form singlet oxygen and the singlet oxygen releasing agent in its oxygen-free form.

Embodiment 7 provides the nanoparticle of any of Embodiments 1-6, wherein the singlet oxygen releasing agent in its oxygen-loaded form comprises one or more pyridone-derived endoperoxides.

Embodiment 8 provides the nanoparticle of any of Embodiments 1-7, which has a size in the range of from 200 nm to 400 nm.

Embodiment 9 provides the nanoparticle of any of Embodiments 1-8, which, when excited, emit fluorescence in the near-infrared range of the electromagnetic spectrum.

Embodiment 10 provides the nanoparticle of any of Embodiments 1-9, which has a fluorescence emission wavelength comprising 670 nm.

Embodiment 11 provides the nanoparticle of any of Embodiments 1-10, which emit luminescence in the near-infrared range of the electromagnetic spectrum.

Embodiment 12 provides the nanoparticle of any of Embodiments 1-11, which has a luminescence emission wavelength comprising 670 nm.

Embodiment 13 provides the nanoparticle of any of Embodiments 1-12, wherein the chitosan-based nanoparticle (CNP) has a size of below 400 nm.

Embodiment 14 provides the nanoparticle of any of Embodiments 1-13, which is further conjugated with polyethylene glycol (PEG).

Embodiment 15 provides the nanoparticle of any of Embodiments 1-14, which is further conjugated with at least one small-molecule targeting ligand.

Embodiment 16 provides the nanoparticle of Embodiment 15, wherein the at least one small-molecule targeting ligand comprises one or more ligands selected from the group consisting of: folate-polyethylene glycol (PEG), PSMAi-PEG, and bis-Zn-DPA-PEG.

Embodiment 17 provides a method of detecting or imaging a tumor in a subject comprising: administering to the subject an amount of at least one nanoparticle of any of Embodiments 1-16, imaging the subject using an optical imaging detection modality, and detecting or imaging a tumor in the subject.

Embodiment 18 provides the method of Embodiment 17, wherein the tumor is a prostate tumor.

Embodiment 19 provides the method of any of Embodiments 17-18, wherein the tumor is selected from the group consisting of a prostate tumor, rectum tumor, colon tumor, uterus tumor, pancreas tumor, and lung tumor.

Embodiment 20 provides the method of any of Embodiments 17-19, wherein the subject is a human.

Embodiment 21 provides the method of any of Embodiments 17-20, wherein the nanoparticles are administered intravenously.

Embodiment 22 provides the method of any of Embodiments 17-21, wherein the nanoparticles are PEGylated.

Embodiment 23 provides the method of any of Embodiments 17-22, wherein the nanoparticles comprise at least one targeting ligand selected from the group consisting of: folate-polyethylene glycol (PEG), PSMAi-PEG, and bis-Zn-DPA-PEG.

Embodiment 24 provides the method of any of Embodiments 17-23, wherein the optical imaging detection modality comprises a chemiluminescence detector.

Embodiment 25 provides a method for fabricating a dual-modality optical imaging nanoparticle, the method comprising: a) reacting chlorin e6 (Ce6) and chitosan, under conditions that allow for coupling of Ce6 to chitosan; b)

reacting a derivatized singlet oxygen releasing agent with the Ce6-coupled chitosan under conditions that allow for coupling of the derivatized singlet oxygen releasing agent to the Ce6-coupled chitosan; and c) isolating the resulting Ce6-coupled, derivatized singled oxygen releasing agent-coupled, chitosan.

Embodiment 26 provides the method of Embodiment 25, wherein the method further comprises: d) irradiating the Ce6-coupled, derivatized singled oxygen releasing agent-coupled, glycol chitosan in the presence of oxygen and radiation, thus forming the singlet oxygen releasing agent in its oxygen-loaded form.

Embodiment 27 provides the method of any of Embodiments 25-26, wherein the derivatized singlet oxygen releasing agent is a pyridone derivative.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A chitosan-based nanoparticle comprising a glycol chitosan nanoparticle conjugated to (i) a photosensitizer, (ii) a targeting ligand, and (iii) a singlet oxygen releasing agent, wherein the singlet oxygen releasing agent exists in an oxygen-free form or in an oxygen-loaded form, wherein the targeting ligand comprises folate, PSMAi, or bis-Zn-DPA, wherein the photosensitizer conjugated to the glycol chitosan has the chemical structure:

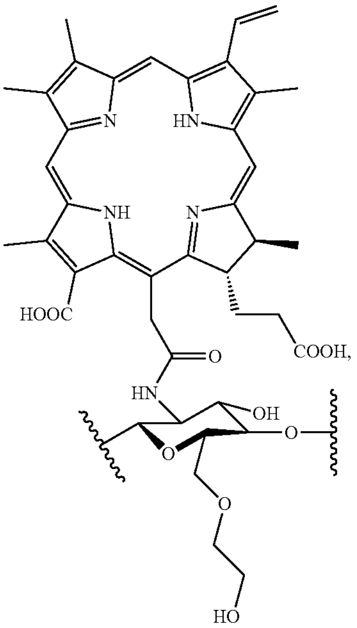

wherein the nanoparticle is configured to transfer energy from the singlet oxygen releasing agent to the photosensitizer, wherein the nanoparticle comprises the following chemical structure when the singlet oxygen releasing agent is in the oxygen-free form:

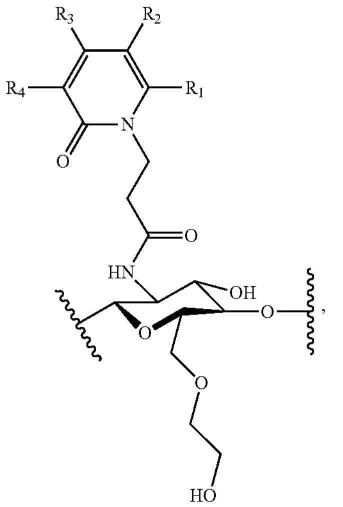

wherein:

$R_3$ is H; and $R_1$, $R_2$, and $R_4$ are each independently H or $CH_3$.

2. The nanoparticle of claim 1, wherein $R_1$ is H, $R_2$ is H, $R_3$ is H, and $R_4$ is H.

3. The nanoparticle of claim 1, wherein the singlet oxygen releasing agent in its oxygen-loaded form comprises the structure:

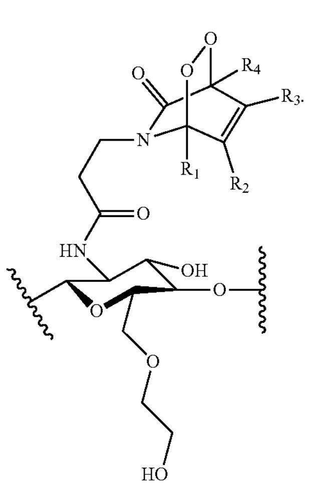

4. The nanoparticle of claim 1, wherein the singlet oxygen releasing agent in its oxygen-free form is configured to react with oxygen under irradiation to form the singlet oxygen releasing agent in its oxygen-loaded form, which decomposes to form singlet oxygen and the singlet oxygen releasing agent in its oxygen-free form.

5. The nanoparticle of claim 1, wherein the nanoparticle has a diameter of 25 to 200 nm.

6. The nanoparticle of claim 1, wherein at least one applies:

(a) wherein when excited, the nanoparticle emits fluorescence at one or more wavelengths in the near-infrared range of the electromagnetic spectrum;

(b) wherein the nanoparticle emits luminescence at one or more wavelengths in the (b) near-infrared range of the electromagnetic spectrum.

7. The nanoparticle of claim 6, which has a fluorescence or luminescence emission wavelength of 650 to 900 nm.

8. The nanoparticle of claim 1, wherein the targeting ligand further comprises polyethylene glycol (PEG).

9. The nanoparticle of claim 1, wherein:

$R_3$ is H; and one of the following combinations applies:

$R_1$ and $R_2$ are H, and $R_4$ is CH3;

$R_1$ is $CH_3$, and $R_2$ and $R_4$ are H;

$R_1$ is $CH_3$, and $R_2$ and $R_4$ are H;

R2 is $CH_3$, and $R_1$ and $R_4$ are H;

R2 is H, and $R_1$ and $R_4$ are $CH_3$; or $R_1$ is $CH_3$, $R_2$ is $CH_3$, and $R_4$ is $CH_3$.

10. The nanoparticle of claim 9, wherein the targeting ligand has the structure:

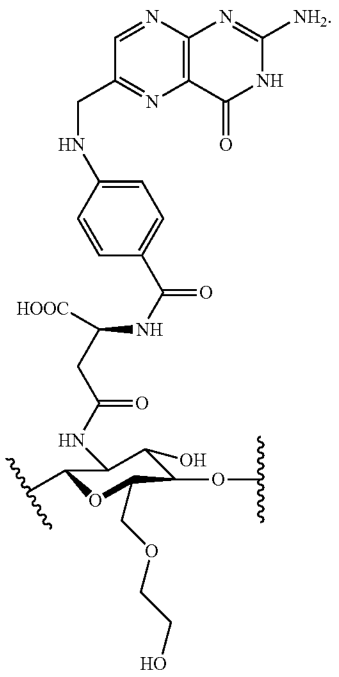

* * * * *